United States Patent
Staskawicz et al.

(10) Patent No.: US 11,891,612 B2
(45) Date of Patent: Feb. 6, 2024

(54) ZAR1 AND JIM2 MEDIATE RESISTANCE AGAINST PLANT PATHOGENS CONTAINING YOPJ-FAMILY EFFECTORS

(71) Applicant: The Regents of the University of California, Oakland, CA (US)

(72) Inventors: Brian J. Staskawicz, Berkeley, CA (US); Alexander Christiaan Schultink, Williamston, MI (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/973,743

(22) PCT Filed: May 24, 2019

(86) PCT No.: PCT/US2019/033962
§ 371 (c)(1),
(2) Date: Dec. 9, 2020

(87) PCT Pub. No.: WO2020/005429
PCT Pub. Date: Jan. 2, 2020

(65) Prior Publication Data
US 2021/0310019 A1    Oct. 7, 2021

Related U.S. Application Data

(60) Provisional application No. 62/692,537, filed on Jun. 29, 2018.

(51) Int. Cl.
*C12N 15/82* (2006.01)
*C07K 14/415* (2006.01)

(52) U.S. Cl.
CPC ........ *C12N 15/8281* (2013.01); *C07K 14/415* (2013.01)

(58) Field of Classification Search
None
See application file for complete search history.

(56) References Cited

U.S. PATENT DOCUMENTS

2004/0016029 A1   1/2004   Wei et al.
2010/0043097 A1   2/2010   Wang et al.

OTHER PUBLICATIONS

Sharlach, M. "Mapping and Identification of the RXopJ4 Resistance Gene and the Search for New Sources of Durable Resistance to Bacterial Spot Disease of Tomato". University of California Berkeley. Dissertation. (Year: 2013).*
Wang et al. "*Arabidopsis* ZED1-related kinases mediate the temperature sensitive intersection of immune response and growth homeostasis". New Phytologist. 215: 711-724. (Year: 2017).*
Sharlach, Molly. "Mapping and Identification of the RXopJ4 Resistance Gene and the Search for New Sources of Durable Resistance to Bacterial Spot Disease of Tomato." Dissertation. UC Davis. 2013 (Year: 2013).*
NCBI Reference Sequence: XP_019243175 (Year: 2016).*
NCBI Reference Sequence: XP_009798868 (Year: 2014).*
Astua-Monge et al., "Xv4-vrxv4: A New Gene-for-Gene Interaction Identified Between Xanthomonas campestris pv. vesicatoria Race T3 and the Wild Tomato Relative *Lycopersicon pennellii*", Molecular Plant-Microbe Interactions, 2000, 13(12): 1346-1355.
Deslandes et al., "Physical interaction between RRS1-R, a protein conferring resistance to bacterial wilt, and PopP2, a type III effector targeted to the plant nucleus", PNAS, 2003, 100(13): 8024-8029.
Rufian et al., "Auto-acetylation on K289 is not essential for HopZ1a-mediated plant defense suppression", Frontiers in Microbiology, 2015, 6: Article 684, pp. 1-12.
Schultink et al., "Using forward genetics in Nicotiana benthamiana to uncover the immune signaling pathway mediating recognition of the Xanthomonas perforans effector XopJ4", New Phytologist, 2019, 221: 1001-1009.
Sharlach et al., "Fine genetic mapping of RXopJ4, a bacterial spot disease resistance locus from Solanum pennellii LA716", Theor. Appl. Genet., 2013, 126: 601-609.
Sharlach, "Mapping and Identification of the RXopJ4 Resistance Gene and the Search for New Sources of Durable Resistance to Bacterial Spot Disease of Tomato", University of California at Berkeley, Dissertation, 2013, pp. 1-89.
Bentham et al., "Animal NLRs provide structural insights into plant NLR function", Annals of Botany, 2017, 119: 689-702.
Lewis et al., "The *Arabidopsis* ZED1 pseudokinase is required for ZAR1-mediated immunity induced by the Pseudomonas syringae type III effector HopZ1a", PNAS, 2013, 110(46): 18722-18727.
Steinbrenner et al., "Effector Recognition and Activation of the *Arabidopsis thaliana* NLR Innate Immune Receptors", Cold Spring Harbor Symposia on Quantitative Biology, vol. LXXVII, 2012, pp. 249-257.
Wilmanski et al., "NLR proteins: integral members of innate immunity and mediators of inflammatory diseases", J Leukoc Biol., 2008, 83(1): 13-30. doi:10.1189/jlb.0607402.

* cited by examiner

*Primary Examiner* — Matthew R Keogh
*Assistant Examiner* — David R Byrnes
(74) *Attorney, Agent, or Firm* — James S. Keddie; Bozicevic, Field & Francis LLP

(57) ABSTRACT

Provided herein is a plant comprising an exogenous polynucleotide encoding a JIM2 polypeptide. In some embodiments, the plants have enhanced resistance to at least one species of *Xanthomonas*.

13 Claims, 10 Drawing Sheets

Specification includes a Sequence Listing.

Transient expression construct

| NbJIM2-deficient *N. benthamiana* | XopJ4 | XopJ4 SpJIM2 |

FIG. 9

A. Disease symptoms

Wild Type ZAR1+JIM2

B. Bacterial growth

```
ATGGATTGCATAAAGAAGATGTGGTCAGTCGTGAAGAAATTTAGGAAGGAAGAAGAAGATGTA
GCAAATCTGTTCCTGCAAAATGGAGGTGCGCTGTTGGAAGAGCTTATTTCTTTTTCTAGTGGA
ACATATGACATTCCAATCCCTAGTTACAGTGCTCAACAACTTGTTAACGCAACAAACAACTTC
TCTGGACGTGTCCATGCTAGCACCTACGGTTACATCTGTAGAGGAACTCTGCAAGGCCACTCT
ATCTTCGTCAAAATGTTCATAAATATTCCAGgtaaccaaccatgtgggttctcaaattaattc
ataatttatttatgcttgttttagcttacatatatggttcacaaagtagtggcagcatg
tactgttagtgtttgtccagattttcgtatcataattgattttcctatctcgtgaagaaagg
ataatatattaccataattgagtttccttttatatgtagaagaaaattataaatcttccat
atttggcgagtccttttcttgctggaaaagtttgaaattctataaattgaagattcgttgc
ttcccattcaacagtatccacaatgtagccataagagatttgagagtcatggttagaggagaa
ctttatgggtcaagggttagtgtaccagttgtgtttgcctcttcgtgaggttgttctttcgat
attttatactcttttttatatagttgattgctcatctctgccatagatatatagattaattga
ccgaatcacgttaatagtatctcttttggtagatttcacttttgttgtctgatttatcgtcgc
taaaggtttgctttactagcttccgcatgatacctaattatttcggtcataacagaaacacag
ttatattgaattaaaatcttggatccacctttgcagGTAACCTTGCCTCACATTCCGAATTTG
ACATTCTTGCTGGAGCTGTACGTGACATTTCAATCACATCTCTAATGAGCGGAAATAAGAATG
TTTTAAAGATTATAGGTTGTTGTTTGGAATTCAGATATCCAgcgcttgtatacgaggacgcgc
gattcgaaaccctcgcaaactttctcgatccgaactgtgacaagttactttcctggaagtgca
ggcttaaaatcgctaagtccatcgctagcgcgatactttacctgcataccgccttccccacgc
ctatcatttataggattttgaatcctcacaatataattctcgatcaccactgtgtaccaaagt
tattcgactttagtttcgtcataagtttgccgccaggggaactcaaggttgaggacgatctta
tctggataccaggatacTTCGATCCAGAGTACCAATCTTCAAGGTTTGTCACTCAAAAGACCG
ACGTCTATAGTTTTGGTGTGCTGCTACTGGTGCTCTTAAATGGACAGGGTCCTATATGCAGGG
CCAATGAAGATGATCCAGAACACATTGTGAATTATGTAAATGACCATATTCACAAGGATGATC
AATTCAAGCACATTGTGGACCCTAAAATCTTGAACGAATCGAGTGTAAATCATCAACAGCTAC
AAGCTTTCATTGATATCGCTTTAAGATGTGTCCAGGCTAAGGGAGAAAATAGACCAGATATGT
TCGAGATTGCAAGAAAGATCCTGCAATTTGAGGATTATAAGGACCATGACGGAGACTATAAGG
ACCATGACCTCGATTATAAGGACGATGACGATAAGTAG
```

FIG. 12

SEQUENCE LISTING

```
<160> NUMBER OF SEQ ID NOS: 92

<210> SEQ ID NO 1
<211> LENGTH: 345
<212> TYPE: PRT
<213> ORGANISM: Nicotiana benthamiana

<400> SEQUENCE: 1

Met Asp Cys Ile Lys Lys Met Trp Ser Val Val Lys Lys Phe Arg Lys
1               5                   10                  15

Glu Glu Glu Asp Val Ala Asn Leu Phe Leu Gln Asn Gly Gly Ala Leu
            20                  25                  30

Leu Glu Glu Leu Ile Ser Phe Ser Ser Gly Thr Tyr Asp Ile Pro Ile
        35                  40                  45

Pro Ser Tyr Ser Ala Gln Gln Leu Val Asn Ala Thr Asn Asn Phe Ser
    50                  55                  60

Gly Arg Val His Ala Ser Thr Tyr Gly Tyr Ile Cys Arg Gly Thr Leu
65                  70                  75                  80

Gln Gly His Ser Ile Phe Val Lys Met Phe Ile Asn Ile Pro Gly Asn
                85                  90                  95

Leu Ala Ser His Ser Glu Phe Asp Ile Leu Ala Gly Ala Val Arg Asp
            100                 105                 110

Ile Ser Ile Thr Ser Leu Met Ser Gly Asn Lys Asn Val Leu Lys Ile
        115                 120                 125

Ile Gly Cys Cys Leu Glu Phe Arg Tyr Pro Ala Leu Val Tyr Glu Asp
    130                 135                 140

Ala Arg Phe Glu Thr Leu Ala Asn Phe Leu Asp Pro Asn Cys Asp Lys
145                 150                 155                 160

Leu Leu Ser Trp Lys Cys Arg Leu Lys Ile Ala Lys Ser Ile Ala Ser
                165                 170                 175
```

```
Ala Ile Leu Tyr Leu His Thr Ala Phe Pro Thr Pro Ile Ile Tyr Arg
            180                 185                 190

Ile Leu Asn Pro His Asn Ile Ile Leu Asp His His Cys Val Pro Lys
            195                 200                 205

Leu Phe Asp Phe Ser Phe Val Ile Ser Leu Pro Pro Gly Glu Leu Lys
            210                 215                 220

Val Glu Asp Asp Leu Ile Trp Ile Pro Gly Tyr Phe Asp Pro Glu Tyr
225                 230                 235                 240

Gln Ser Ser Arg Phe Val Thr Gln Lys Thr Asp Val Tyr Ser Phe Gly
            245                 250                 255

Val Leu Leu Leu Val Leu Leu Asn Gly Gln Gly Pro Ile Cys Arg Ala
            260                 265                 270

Asn Glu Asp Asp Pro Glu His Ile Val Asn Tyr Val Asn Asp His Ile
            275                 280                 285

His Lys Asp Asp Gln Phe Lys His Ile Val Asp Pro Lys Ile Leu Asn
            290                 295                 300

Glu Ser Ser Val Asn His Gln Gln Leu Gln Ala Phe Ile Asp Ile Ala
305                 310                 315                 320

Leu Arg Cys Val Gln Ala Lys Gly Glu Asn Arg Pro Asp Met Phe Glu
            325                 330                 335

Ile Ala Arg Lys Ile Leu Gln Phe Glu
            340                 345

<210> SEQ ID NO 2
<211> LENGTH: 365
<212> TYPE: PRT
<213> ORGANISM: Solanum pennellii

<400> SEQUENCE: 2

Met Gln Phe Phe Arg Glu Leu Thr Ile Arg Lys Lys Gln Ser Leu Ser
1               5                   10                  15

Glu Glu Trp Arg Lys Lys Glu His Asp Tyr Tyr Leu His Asn Gly Ser
            20                  25                  30

Ala Val Leu Glu Glu Leu Leu Ala Leu Cys Asn Gly Asn Cys Arg Ile
            35                  40                  45

Pro Ile Arg Tyr Phe Thr Ala Ser Glu Ile Asp Asp Ala Ile Ser Tyr
        50                  55                  60

Ser Gln Asn Glu Leu Glu Ile Phe Asp Gly Arg Met Val Ala Gly Ser
65                  70                  75                  80

Met Asp Lys Arg Leu Val Phe Val Arg Phe Pro Asn Tyr Phe Arg
            85                  90                  95

Asn Phe Phe Asn Ile Phe Arg Asp Ile Ala Ile Thr Ala Gln Met Ser
            100                 105                 110

His Leu Lys Asn Val Leu Arg Leu Val Gly Cys Cys Val Glu Phe Glu
            115                 120                 125

Lys Pro Val Met Val Tyr Glu Tyr Val Glu Ala Ile Ser Leu His Thr
            130                 135                 140

Leu Leu Phe Glu Lys Gly Asn His Asp Asp Gln Thr Arg Lys Ser Leu
145                 150                 155                 160

Leu Ser Trp Gly Asn Arg Leu Arg Ile Ala Asn Glu Val Ala Ser Ala
            165                 170                 175

Val Val Phe Leu His Thr Glu Phe Thr Thr Pro Ile Ile Tyr Lys Asp
            180                 185                 190

Leu Lys Pro Ser Asn Val Ile Ile Asp Gln Asn Ser Gly Val Ala Lys
            195                 200                 205
```

```
Leu Leu Asn Phe Ser Leu Ser Val Ser Leu Pro Gly Glu Leu Gln
    210                 215                 220

Val Ile Lys Asp Val Thr Cys Gly Thr Tyr Gly Tyr Leu Ala Pro Glu
225                 230                 235                 240

Tyr Ala Val Ser Gly Ile Val Thr Gln Asn Thr Asp Val Tyr Ser Phe
                245                 250                 255

Gly Val Val Leu Leu Gln Leu Leu Thr Gly Lys Asn Met Gly Thr Leu
                260                 265                 270

Asp Ile Lys Asp Arg Lys Tyr Ile Met Tyr Asp Val Glu Ser Asp Leu
        275                 280                 285

Asp Pro Ile Asp Ile Glu Lys Ile Tyr Val Met Asp Ile Ala Asp Lys
    290                 295                 300

Ala Ile Leu Glu Glu Tyr Gly Ile Glu Ile Gln Gln Gln Leu Glu Asp
305                 310                 315                 320

Cys Trp Asp Leu Val Lys Lys Cys Thr Lys Ser Lys Gly Glu Glu Arg
                325                 330                 335

Pro Tyr Met Ile Glu Val Ala Lys Glu Leu Arg Arg Ile Tyr Asn Cys
                340                 345                 350

Phe Arg Val Leu Thr Leu Gly Gln Asn Gln Leu His Lys
            355                 360                 365

<210> SEQ ID NO 3
<211> LENGTH: 845
<212> TYPE: PRT
<213> ORGANISM: Nicotiana benthamiana

<400> SEQUENCE: 3

Met Val Asp Ala Val Val Thr Val Phe Leu Glu Lys Leu Leu His Val
1               5                   10                  15

Leu Thr Glu Glu Ser Arg Phe Leu Thr Lys Tyr Arg Gln Gln Phe Glu
                20                  25                  30

Lys Leu Lys Asn Glu Leu Leu Phe Met Gln Ser Phe Leu Lys Asp Ala
            35                  40                  45

Glu Arg Leu Lys Arg Lys Asn Asn Thr Leu Lys Gly Val Met Ser Cys
50                  55                  60

Leu Arg Asp Leu Ile Phe Glu Ala Glu Ile Leu Glu Asp Cys Gln
65                  70                  75                  80

Asn Gln Ser Ala Asp Ser Asp Arg Ala Thr Thr Cys Phe His Pro Lys
                85                  90                  95

Arg Leu Ser Leu Arg His Gln Thr Gly Lys Cys Leu Ala Lys Ile Asn
            100                 105                 110

Asp Arg Ile Ser Glu Ile Lys Gln Asn Ile Ser Thr Tyr Leu Gly Val
        115                 120                 125

Pro Leu Leu Glu Glu Gly Ser Met Glu Ala His Asn Asn Leu Met Ser
    130                 135                 140

Arg Trp Thr Ser Ser Leu Tyr Asp His Thr Gln Val Val Gly Leu Glu
145                 150                 155                 160

Gly Asp Thr Glu Lys Ile Lys Asp Trp Leu Phe Glu Ala Arg Asp Gly
                165                 170                 175

Leu Leu Thr Ile Ala Phe Val Gly Met Gly Gly Leu Gly Lys Thr Thr
                180                 185                 190

Leu Ala Gln Lys Val Phe Asn Asp Lys Arg Val Glu Asp His Leu Glu
        195                 200                 205

Arg Arg Ile Trp Val Ser Val Ser Gln Thr Phe Thr Glu Glu Gln Val
```

```
                210                 215                 220
Met Arg Ser Ile Leu Arg Ser Leu Gly Asp Ala Cys Val Gly Asp Asp
225                 230                 235                 240

Gln Cys Glu Leu Leu Arg Lys Ile Asn Gln Tyr Leu Leu Gly Lys Arg
                245                 250                 255

Phe Leu Ile Val Met Asp Asp Val Trp Ser Trp Asp Asn Ala Trp Trp
                260                 265                 270

Gln Lys Ile Tyr Thr Gly Leu Pro Lys Gly Asn Gly Ser Thr Val Ile
                275                 280                 285

Val Thr Thr Arg Asn Glu Leu Val Ala Arg Lys Met Gly Val Thr Glu
                290                 295                 300

Ala Arg Ile His Trp Pro Lys Phe Leu Asn Glu His Tyr Ser Trp Leu
305                 310                 315                 320

Leu Phe Arg Lys Ile Ala Phe Ala Gly Ser Ala Gly Glu Cys His Phe
                325                 330                 335

Pro Glu Leu Glu Asp Val Gly Lys Glu Ile Val Glu Lys Cys Lys Gly
                340                 345                 350

Leu Pro Leu Ala Ile Lys Ala Val Gly Gly Val Met Leu Cys Lys Pro
                355                 360                 365

Ser Tyr Tyr His Glu Trp Arg Arg Ile Ser Asn His Phe Arg Asp Glu
370                 375                 380

Leu Lys Glu Asn Asp Asp Ser Val Met Ala Ser Leu Gln Leu Ser Tyr
385                 390                 395                 400

Asp Glu Leu Pro Pro Tyr Leu Lys Ser Cys Phe Leu Cys Phe Ser Leu
                405                 410                 415

Phe Pro Glu Asp Cys Val Ile Pro Lys Asp Gln Leu Ile Arg Trp Trp
                420                 425                 430

Ile Gly Glu Gly Phe Ile Pro Leu Arg Ser Gly Arg Leu Ser Thr Glu
                435                 440                 445

Val Gly Glu Asp Cys Phe Ser Gln Leu Ser Asn Arg Cys Leu Ile Glu
                450                 455                 460

Val Val Asp Lys Ala Tyr Asn Gly Val Ile His Thr Cys Lys Met His
465                 470                 475                 480

Asp Met Val Arg Asp Leu Val Ile Lys Leu Ala Glu Asp Ala Phe
                485                 490                 495

Phe Thr Pro Ala Asp Ala Thr Cys Arg His Leu Gly Ile Lys Ser Glu
                500                 505                 510

Met Asn Trp Lys Gln Leu Leu Ser Asn Gln Lys Leu Arg Ala Leu Leu
                515                 520                 525

Thr Thr Thr Lys Ser Gly Glu Val Asn Lys Ile His Ser Asp Ile Ala
                530                 535                 540

Lys Lys Leu Cys Lys Ser Arg His Leu Gln Val Leu Asp Leu Ser Lys
545                 550                 555                 560

Ser Ile Phe Asp Val Pro Leu Ser Ser Leu Leu Glu Gly Ile Gly Ser
                565                 570                 575

Ala Lys Gln Leu Thr Tyr Leu Ser Leu Ser Asn Thr His Pro Met Ile
                580                 585                 590

Gly Val Pro Ala Ser Ile Ser Lys Leu Glu Lys Leu Gln Ile Leu Asp
                595                 600                 605

Phe Ser Tyr Cys Gln Asn Met Lys Met Leu Pro Ser Cys Val Leu Thr
                610                 615                 620

Phe Glu Glu Leu Ala Val Leu Asp Val Asn Asn Cys Gly Ser Leu Glu
625                 630                 635                 640
```

-continued

```
Tyr Leu Pro Lys Gly Leu Ser Arg Leu Ser Asn Leu Gln Val Leu Leu
                645                 650                 655

Gly Phe Lys Pro Ala Lys Leu Ser Gln Pro Gly Gly Cys Arg Ile Ala
                660                 665                 670

Glu Leu Arg Ser Leu Thr Arg Leu Arg Thr Leu Ser Leu Arg Leu Thr
                675                 680                 685

Glu Asn Glu Glu Ile Gly Asp Asp Glu Gly Asn Ala Leu Val Asp Leu
                690                 695                 700

Gln Glu Leu Gln Phe Leu Thr Ile Ser Cys Phe Gly Ser Gln Asp Asn
705                 710                 715                 720

Gly Leu Ala Thr Lys Leu Gly Arg Leu Tyr Pro Pro Arg Gln Leu His
                725                 730                 735

Glu Leu Ile Leu Lys Phe Tyr Pro Ser Lys Thr Ser Pro Glu Trp Leu
                740                 745                 750

Asn Pro Asn Leu Ser Pro Met Leu Arg Tyr Leu Ser Ile Ile Ser Gly
                755                 760                 765

Asp Ile Thr Gln Met His Glu Asn Phe Trp Gly Asp Gly Ser Thr Ala
                770                 775                 780

Trp Lys Ile Glu Gly Leu Met Leu Glu Ser Leu Ser Asp Leu Arg Leu
785                 790                 795                 800

Glu Trp Ser Ala Met His Gln Val Met Pro Ser Leu Arg Ile Leu Lys
                805                 810                 815

Val Ser Trp Cys Pro Glu Leu Glu Ser Phe Pro Ile Glu Asp Ala Gly
                820                 825                 830

Phe Arg Gly Gly Leu Trp Lys Lys Glu His Arg Asn
                835                 840                 845

<210> SEQ ID NO 4
<211> LENGTH: 850
<212> TYPE: PRT
<213> ORGANISM: Solanum pennellii

<400> SEQUENCE: 4

Met Val Asp Ala Val Val Thr Val Phe Leu Glu Lys Leu Leu Asn Val
1               5                   10                  15

Leu Thr Glu Glu Ser Arg Phe Leu Ser Gln His Arg Gln Gln Phe Glu
                20                  25                  30

Lys Leu Lys Asn Glu Leu Leu Phe Met Gln Ser Phe Leu Lys Asp Ala
                35                  40                  45

Glu Arg Leu Lys Arg Lys His Thr Thr Leu Lys Thr Val Met Ala Cys
        50                  55                  60

Leu Arg Asp Leu Ile Phe Glu Ala Glu Ile Leu Glu Asp Cys Gln
65                  70                  75                  80

Asn Gln Ser Ala Asp Ser Asp Gly Ser Thr Arg Phe Ser Thr Arg Leu
                85                  90                  95

His Pro Lys Arg Leu Ser His Arg His Gln Thr Gly Lys Arg Leu Ser
                100                 105                 110

Glu Ile Asn Asp Lys Ile Thr Glu Ile Lys Gln Asn Ile Ser Thr Tyr
                115                 120                 125

Leu Gly Val Pro Leu Met Lys Glu Gly Ser Met Glu Ala His Asp Asn
                130                 135                 140

Leu Met Thr Arg Trp Thr Ser Ser Leu Tyr Asp His Thr Gln Val Val
145                 150                 155                 160

Gly Leu Glu Gly Asp Thr Glu Lys Ile Lys Asp Trp Leu Phe Glu Ala
```

```
            165                 170                 175
Ser Asp Gly Leu Leu Ala Val Ala Phe Val Gly Met Gly Leu Gly
            180                 185                 190

Lys Thr Thr Leu Ala Gln Lys Val Phe Asn Glu Arg Ser Met Glu Asn
            195                 200                 205

His Phe Glu Arg Arg Ile Trp Val Ser Val Ser Gln Thr Phe Thr Glu
210                 215                 220

Glu Gln Val Met Arg Ser Ile Leu Lys Thr Leu Gly Asp Ala Cys Ile
225                 230                 235                 240

Gly Asp Asp Gln Gly Glu Leu Leu Arg Lys Ile Asn Gln Tyr Leu Leu
                245                 250                 255

Gly Lys Arg Phe Leu Ile Val Met Asp Asp Val Trp Ser Leu Asp Asn
                260                 265                 270

Ala Trp Trp Gln Lys Ile Tyr Ser Gly Leu Pro Lys Gly Asn Gly Ser
                275                 280                 285

Ser Val Ile Val Thr Thr Arg Asn Glu Leu Val Ala Arg Lys Met Gly
                290                 295                 300

Val Thr Glu Ala Arg Thr His Trp Pro Lys Phe Leu Asn Glu His Tyr
305                 310                 315                 320

Ser Trp Leu Leu Phe Arg Lys Ile Ala Phe Ala Ala Thr Ala Gly Glu
                325                 330                 335

Cys Asp Phe Pro Glu Leu Glu Asp Val Gly Lys Glu Ile Val Glu Lys
                340                 345                 350

Cys Lys Gly Leu Pro Leu Ala Ile Lys Ala Val Gly Gly Val Met Leu
                355                 360                 365

Cys Lys Pro Pro Tyr Tyr His Glu Trp Arg Arg Ile Ala Asp His Phe
                370                 375                 380

Arg Asp Glu Leu Lys Glu Asn Asp Asn Ser Val Met Ala Ser Leu Gln
385                 390                 395                 400

Leu Ser Tyr Asp Glu Leu Pro Pro Tyr Leu Lys Ser Cys Phe Leu Cys
                405                 410                 415

Phe Ser Leu Phe Pro Glu Asp Cys Val Ile Leu Lys Asp Gln Leu Ile
                420                 425                 430

Arg Trp Trp Ile Gly Glu Ser Phe Ile Pro Leu Arg Ser Gly Arg Leu
                435                 440                 445

Ser Thr Glu Val Gly Glu Asp Cys Phe Ser Gln Leu Ser Asn Arg Cys
                450                 455                 460

Leu Ile Glu Val Val Asp Lys Ala Tyr Asn Gly Val Ile His Thr Cys
465                 470                 475                 480

Lys Met His Asp Met Val Arg Asp Leu Val Ile Lys Ile Ala Asp Asp
                    485                 490                 495

Asp Ser Phe Ser Thr Pro Ser Asp Ala Asn Cys Arg His Leu Gly Ile
                500                 505                 510

Asn Ser Ala Met Asn Gly Lys Gln Leu Leu Ser Asn Arg Lys Leu Arg
                515                 520                 525

Ala Leu Leu Thr Thr Thr Lys Ser Gly Glu Val Asn Lys Ile Pro Ser
                530                 535                 540

Asp Ile Ala Lys Lys Phe Cys Asn Ser Arg His Leu Gln Val Leu Asp
545                 550                 555                 560

Leu Ser Lys Ser Ile Phe Asp Val Pro Leu Ser Ser Leu Leu Glu Gly
                    565                 570                 575

Ile Gly Ser Ala Arg Gln Leu Ala Tyr Leu Ser Leu Ser Asn Thr His
                580                 585                 590
```

```
Pro Leu Ile Gly Val Pro Asp Ser Ile Ser Asn Leu Glu Lys Leu Gln
            595                 600                 605

Ile Leu Asp Phe Ser Tyr Cys Gln Asn Met Lys Met Leu Pro Ser Cys
610                 615                 620

Val Leu Thr Phe Val Glu Leu Ala Ile Leu Asp Leu Asn His Cys Gly
625                 630                 635                 640

Ser Leu Glu Tyr Leu Pro Lys Gly Leu Ser Lys Leu Ser Asn Leu Gln
            645                 650                 655

Val Leu Leu Gly Phe Lys Pro Ala Lys Leu Ser Gln Arg Gly Gly Cys
            660                 665                 670

Arg Ile Ser Glu Leu Arg Ser Leu Thr Arg Leu Arg Leu Ser Leu
            675                 680                 685

Arg Leu Thr Gln Asp Glu Glu Ile Gly Asp Asp Glu Gly Asn Ala Leu
690                 695                 700

Ile Gly Leu Gln Glu Leu Gln Phe Leu Thr Ile Ser Cys Phe Asp Ser
705                 710                 715                 720

Gln Asp Asp Gly Leu Val Thr Lys Leu Gly Lys Leu Tyr Pro Pro Arg
                725                 730                 735

Gln Leu His Glu Leu Ile Leu Lys Phe Tyr Pro Gly Lys Ile Ser Pro
            740                 745                 750

Glu Trp Leu Asn Pro Thr Ser Leu Pro Met Leu Arg Tyr Met Ser Ile
            755                 760                 765

Val Ser Gly Asp Met Lys Glu Met His Asp Asn Phe Trp Gly Asp His
            770                 775                 780

Ser Thr Phe Trp Lys Ile Glu Gly Leu Met Leu Glu Ala Leu Thr Asp
785                 790                 795                 800

Leu Arg Leu Glu Trp Ser Ala Ile Asn Arg Val Met Pro Ser Leu Arg
                805                 810                 815

Ile Leu Lys Ala Ser Trp Cys Pro Glu Val Glu Ala Phe Pro Ile Glu
            820                 825                 830

Asp Ala Gly Phe Arg Gly Gly Leu Trp Lys Lys Glu Glu His Ser His
            835                 840                 845

Arg Cys
    850

<210> SEQ ID NO 5
<211> LENGTH: 27
<212> TYPE: DNA
<213> ORGANISM: Artificial sequence
<220> FEATURE:
<223> OTHER INFORMATION: synthetic sequence

<400> SEQUENCE: 5
tggtctccga gcatggtgga cgcagtg                                           27

<210> SEQ ID NO 6
<211> LENGTH: 33
<212> TYPE: DNA
<213> ORGANISM: Artificial sequence
<220> FEATURE:
<223> OTHER INFORMATION: synthetic sequence

<400> SEQUENCE: 6
tggtctcctt ggtcaacacc tatggctata ttc                                    33

<210> SEQ ID NO 7
<211> LENGTH: 32
```

```
<212> TYPE: DNA
<213> ORGANISM: Artificial sequence
<220> FEATURE:
<223> OTHER INFORMATION: synthetic sequence

<400> SEQUENCE: 7
tggtctccga gcatggtgga cgctgttgta ac                                32

<210> SEQ ID NO 8
<211> LENGTH: 29
<212> TYPE: DNA
<213> ORGANISM: Artificial sequence
<220> FEATURE:
<223> OTHER INFORMATION: synthetic sequence

<400> SEQUENCE: 8
tggtctcctt ggtcaggttc tgtgcaatg                                    29

<210> SEQ ID NO 9
<211> LENGTH: 33
<212> TYPE: DNA
<213> ORGANISM: Artificial sequence
<220> FEATURE:
<223> OTHER INFORMATION: synthetic sequence

<400> SEQUENCE: 9
tggtctccga gcatgagcaa gaacaataag aag                               33

<210> SEQ ID NO 10
<211> LENGTH: 33
<212> TYPE: DNA
<213> ORGANISM: Artificial sequence
<220> FEATURE:
<223> OTHER INFORMATION: synthetic sequence

<400> SEQUENCE: 10
tggtctcctt ggtcaagaga gtttctcaat caa                               33

<210> SEQ ID NO 11
<211> LENGTH: 30
<212> TYPE: DNA
<213> ORGANISM: Artificial sequence
<220> FEATURE:
<223> OTHER INFORMATION: synthetic sequence

<400> SEQUENCE: 11
tggtctccga gcatgggaaa tgtatgcgtc                                   30

<210> SEQ ID NO 12
<211> LENGTH: 28
<212> TYPE: DNA
<213> ORGANISM: Artificial sequence
<220> FEATURE:
<223> OTHER INFORMATION: synthetic sequence

<400> SEQUENCE: 12
tggtctcctt ggttagcgct gctcttcg                                     28

<210> SEQ ID NO 13
<211> LENGTH: 41
<212> TYPE: DNA
<213> ORGANISM: Artificial sequence
<220> FEATURE:
<223> OTHER INFORMATION: synthetic sequence

<400> SEQUENCE: 13
```
aagcctcggt ctccgagcat ggattgcata aagaagatgt g          41

<210> SEQ ID NO 14
<211> LENGTH: 40
<212> TYPE: DNA
<213> ORGANISM: Artificial sequence
<220> FEATURE:
<223> OTHER INFORMATION: synthetic sequence

<400> SEQUENCE: 14
aagcctcggt ctccaagcgc tggatatctg aattccaaac          40

<210> SEQ ID NO 15
<211> LENGTH: 33
<212> TYPE: DNA
<213> ORGANISM: Artificial sequence
<220> FEATURE:
<223> OTHER INFORMATION: synthetic sequence

<400> SEQUENCE: 15
aagcctcggt ctccgcttgt atacgaggac gcg          33

<210> SEQ ID NO 16
<211> LENGTH: 42
<212> TYPE: DNA
<213> ORGANISM: Artificial sequence
<220> FEATURE:
<223> OTHER INFORMATION: synthetic sequence

<400> SEQUENCE: 16
aagcctcggt ctcccgaagt atcctggtat ccagataaga tc          42

<210> SEQ ID NO 17
<211> LENGTH: 36
<212> TYPE: DNA
<213> ORGANISM: Artificial sequence
<220> FEATURE:
<223> OTHER INFORMATION: synthetic sequence

<400> SEQUENCE: 17
aagcctcggt ctccttcgat ccagagtacc aatctt          36

<210> SEQ ID NO 18
<211> LENGTH: 41
<212> TYPE: DNA
<213> ORGANISM: Artificial sequence
<220> FEATURE:
<223> OTHER INFORMATION: synthetic sequence

<400> SEQUENCE: 18
aagcctcggt ctccttggtt actcaaattg caggatcttt c          41

<210> SEQ ID NO 19
<211> LENGTH: 37
<212> TYPE: DNA
<213> ORGANISM: Artificial sequence
<220> FEATURE:
<223> OTHER INFORMATION: synthetic sequence

<400> SEQUENCE: 19
aagcctcggt ctccaaagcg atggattccg gcatagt          37

<210> SEQ ID NO 20
<211> LENGTH: 36
<212> TYPE: DNA
<213> ORGANISM: Artificial sequence
<220> FEATURE:
<223> OTHER INFORMATION: synthetic sequence

<400> SEQUENCE: 20
aagcctcggt ctccttggta agcttgcatg cctgca         36

<210> SEQ ID NO 21
<211> LENGTH: 38
<212> TYPE: DNA
<213> ORGANISM: Artificial sequence
<220> FEATURE:
<223> OTHER INFORMATION: synthetic sequence

<400> SEQUENCE: 21
aagcctcggt ctccgagcag ctgaagaaag agcagtat       38

<210> SEQ ID NO 22
<211> LENGTH: 38
<212> TYPE: DNA
<213> ORGANISM: Artificial sequence
<220> FEATURE:
<223> OTHER INFORMATION: synthetic sequence

<400> SEQUENCE: 22
aagcctcggt ctccttggta agcacactct tgagatga       38

<210> SEQ ID NO 23
<211> LENGTH: 38
<212> TYPE: DNA
<213> ORGANISM: Artificial sequence
<220> FEATURE:
<223> OTHER INFORMATION: synthetic sequence

<400> SEQUENCE: 23
aagcctcggt ctccgagcat acacctgcaa cagacata       38

<210> SEQ ID NO 24
<211> LENGTH: 38
<212> TYPE: DNA
<213> ORGANISM: Artificial sequence
<220> FEATURE:
<223> OTHER INFORMATION: synthetic sequence

<400> SEQUENCE: 24
aagcctcggt ctccttggcg caatctattt tcccaaga       38

<210> SEQ ID NO 25
<211> LENGTH: 38
<212> TYPE: DNA
<213> ORGANISM: Artificial sequence
<220> FEATURE:
<223> OTHER INFORMATION: synthetic sequence

<400> SEQUENCE: 25
aagcctcggt ctccgagcgc actagtgtat gaagatgc       38

<210> SEQ ID NO 26
<211> LENGTH: 38
<212> TYPE: DNA
<213> ORGANISM: Artificial sequence
<220> FEATURE:
<223> OTHER INFORMATION: synthetic sequence

<400> SEQUENCE: 26
aagcctcggt ctccttggat agccaggaat ccaaatca       38

<210> SEQ ID NO 27
<211> LENGTH: 38
<212> TYPE: DNA
<213> ORGANISM: Artificial sequence
<220> FEATURE:
<223> OTHER INFORMATION: synthetic sequence

<400> SEQUENCE: 27
aagcctcggt ctccgagcag agttaaccat gagggaaa                              38

<210> SEQ ID NO 28
<211> LENGTH: 38
<212> TYPE: DNA
<213> ORGANISM: Artificial sequence
<220> FEATURE:
<223> OTHER INFORMATION: synthetic sequence

<400> SEQUENCE: 28
aagcctcggt ctccttggag aagacactcc attgtagg                              38

<210> SEQ ID NO 29
<211> LENGTH: 39
<212> TYPE: DNA
<213> ORGANISM: Artificial sequence
<220> FEATURE:
<223> OTHER INFORMATION: synthetic sequence

<400> SEQUENCE: 29
atactgcagg agctcggtac catggtggat gcggtggtc                             39

<210> SEQ ID NO 30
<211> LENGTH: 43
<212> TYPE: DNA
<213> ORGANISM: Artificial sequence
<220> FEATURE:
<223> OTHER INFORMATION: synthetic sequence

<400> SEQUENCE: 30
tgccaaatgt ttgaacgatc gtcagttcct atgttcttcc ttc                        43

<210> SEQ ID NO 31
<211> LENGTH: 23
<212> TYPE: DNA
<213> ORGANISM: Artificial sequence
<220> FEATURE:
<223> OTHER INFORMATION: synthetic sequence

<400> SEQUENCE: 31
ctgtttgcga gacttaatct ttg                                              23

<210> SEQ ID NO 32
<211> LENGTH: 23
<212> TYPE: DNA
<213> ORGANISM: Artificial sequence
<220> FEATURE:
<223> OTHER INFORMATION: synthetic sequence

<400> SEQUENCE: 32
gctcagaaag tcttcaatga caa                                              23

<210> SEQ ID NO 33
<211> LENGTH: 20
<212> TYPE: DNA
<213> ORGANISM: Artificial sequence
<220> FEATURE:
<223> OTHER INFORMATION: synthetic sequence

```
<400> SEQUENCE: 33
ttcttggcaa tgtcggaatg                                                  20

<210> SEQ ID NO 34
<211> LENGTH: 22
<212> TYPE: DNA
<213> ORGANISM: Artificial sequence
<220> FEATURE:
<223> OTHER INFORMATION: synthetic sequence

<400> SEQUENCE: 34
ggaagcaact attgagcaat ca                                               22

<210> SEQ ID NO 35
<211> LENGTH: 24
<212> TYPE: DNA
<213> ORGANISM: Artificial sequence
<220> FEATURE:
<223> OTHER INFORMATION: synthetic sequence

<400> SEQUENCE: 35
gcttatgttt ttcaatctct ggac                                             24

<210> SEQ ID NO 36
<211> LENGTH: 20
<212> TYPE: DNA
<213> ORGANISM: Artificial sequence
<220> FEATURE:
<223> OTHER INFORMATION: synthetic sequence

<400> SEQUENCE: 36
gtttctttca cttgctcctt                                                  20

<210> SEQ ID NO 37
<211> LENGTH: 20
<212> TYPE: DNA
<213> ORGANISM: Artificial sequence
<220> FEATURE:
<223> OTHER INFORMATION: synthetic sequence

<400> SEQUENCE: 37
ttctcatgac ttgttcctca                                                  20

<210> SEQ ID NO 38
<211> LENGTH: 17
<212> TYPE: DNA
<213> ORGANISM: Artificial sequence
<220> FEATURE:
<223> OTHER INFORMATION: synthetic sequence

<400> SEQUENCE: 38
gaatggcata cgggacg                                                     17

<210> SEQ ID NO 39
<211> LENGTH: 20
<212> TYPE: DNA
<213> ORGANISM: Artificial sequence
<220> FEATURE:
<223> OTHER INFORMATION: synthetic sequence

<400> SEQUENCE: 39
attgcggaga gttatcagaa                                                  20

<210> SEQ ID NO 40
```

```
<211> LENGTH: 19
<212> TYPE: DNA
<213> ORGANISM: Artificial sequence
<220> FEATURE:
<223> OTHER INFORMATION: synthetic sequence

<400> SEQUENCE: 40
cgcgaaaatg ttcgtcaag                                                  19

<210> SEQ ID NO 41
<211> LENGTH: 44
<212> TYPE: DNA
<213> ORGANISM: Artificial sequence
<220> FEATURE:
<223> OTHER INFORMATION: synthetic sequence

<400> SEQUENCE: 41
tttgtacaaa aaagcaggct ccgcggcggg acgatctggg cact                      44

<210> SEQ ID NO 42
<211> LENGTH: 47
<212> TYPE: DNA
<213> ORGANISM: Artificial sequence
<220> FEATURE:
<223> OTHER INFORMATION: synthetic sequence

<400> SEQUENCE: 42
gactcaacgc atgacgaatg gatccttcat cgatcaagtc cgtataa                   47

<210> SEQ ID NO 43
<211> LENGTH: 44
<212> TYPE: DNA
<213> ORGANISM: Artificial sequence
<220> FEATURE:
<223> OTHER INFORMATION: synthetic sequence

<400> SEQUENCE: 43
tacggacttg atcgatgaag gatccattcg tcatgcgttg agtc                      44

<210> SEQ ID NO 44
<211> LENGTH: 43
<212> TYPE: DNA
<213> ORGANISM: Artificial sequence
<220> FEATURE:
<223> OTHER INFORMATION: synthetic sequence

<400> SEQUENCE: 44
tacaagaaag ctgggtcggc gcgcccagaa agccgacgct gct                       43

<210> SEQ ID NO 45
<211> LENGTH: 20
<212> TYPE: DNA
<213> ORGANISM: Artificial sequence
<220> FEATURE:
<223> OTHER INFORMATION: synthetic sequence

<400> SEQUENCE: 45
gtgtatagat tcccgctgaa                                                 20

<210> SEQ ID NO 46
<211> LENGTH: 20
<212> TYPE: DNA
<213> ORGANISM: Artificial sequence
<220> FEATURE:
<223> OTHER INFORMATION: synthetic sequence

<400> SEQUENCE: 46
```
tcttccatat ttggcgagtc                                              20

<210> SEQ ID NO 47
<211> LENGTH: 20
<212> TYPE: DNA
<213> ORGANISM: Artificial sequence
<220> FEATURE:
<223> OTHER INFORMATION: synthetic sequence

<400> SEQUENCE: 47
tctccactga gtctgaaaac                                              20

<210> SEQ ID NO 48
<211> LENGTH: 36
<212> TYPE: DNA
<213> ORGANISM: Artificial sequence
<220> FEATURE:
<223> OTHER INFORMATION: synthetic sequence

<400> SEQUENCE: 48
atggtctcct tgggcccatc ctttcttta tgaaca                             36

<210> SEQ ID NO 49
<211> LENGTH: 29
<212> TYPE: DNA
<213> ORGANISM: Artificial sequence
<220> FEATURE:
<223> OTHER INFORMATION: synthetic sequence

<400> SEQUENCE: 49
atggtctctg agacctatca gtgcattcc                                    29

<210> SEQ ID NO 50
<211> LENGTH: 29
<212> TYPE: DNA
<213> ORGANISM: Artificial sequence
<220> FEATURE:
<223> OTHER INFORMATION: synthetic sequence

<400> SEQUENCE: 50
atggtctcct ctccaagaac ttcaattct                                    29

<210> SEQ ID NO 51
<211> LENGTH: 31
<212> TYPE: DNA
<213> ORGANISM: Artificial sequence
<220> FEATURE:
<223> OTHER INFORMATION: synthetic sequence

<400> SEQUENCE: 51
atggtctccg tcaatttatg taacgctctc t                                 31

<210> SEQ ID NO 52
<211> LENGTH: 46
<212> TYPE: DNA
<213> ORGANISM: Artificial sequence
<220> FEATURE:
<223> OTHER INFORMATION: synthetic sequence

<400> SEQUENCE: 52
aatgtactgg ggtggttttg ggcccacccc aaaatttagc taatcg                 46

<210> SEQ ID NO 53
<211> LENGTH: 45
<212> TYPE: DNA

<210> SEQ ID NO 53
<211> LENGTH: 45
<212> TYPE: DNA
<213> ORGANISM: Artificial sequence
<220> FEATURE:
<223> OTHER INFORMATION: synthetic sequence

<400> SEQUENCE: 53
agtcaaattt tccgtgatag ttaacagtgg acaagtcaac ctatt     45

<210> SEQ ID NO 54
<211> LENGTH: 36
<212> TYPE: DNA
<213> ORGANISM: Artificial sequence
<220> FEATURE:
<223> OTHER INFORMATION: synthetic sequence

<400> SEQUENCE: 54
atggtctcct tgggcccatc ctttcttta tgaaca     36

<210> SEQ ID NO 55
<211> LENGTH: 29
<212> TYPE: DNA
<213> ORGANISM: Artificial sequence
<220> FEATURE:
<223> OTHER INFORMATION: synthetic sequence

<400> SEQUENCE: 55
atggtctctg agacctatca gtgcattcc     29

<210> SEQ ID NO 56
<211> LENGTH: 29
<212> TYPE: DNA
<213> ORGANISM: Artificial sequence
<220> FEATURE:
<223> OTHER INFORMATION: synthetic sequence

<400> SEQUENCE: 56
atggtctcct ctccaagaac ttcaattct     29

<210> SEQ ID NO 57
<211> LENGTH: 31
<212> TYPE: DNA
<213> ORGANISM: Artificial sequence
<220> FEATURE:
<223> OTHER INFORMATION: synthetic sequence

<400> SEQUENCE: 57
atggtctccg tcaatttatg taacgctctc t     31

<210> SEQ ID NO 58
<211> LENGTH: 46
<212> TYPE: DNA
<213> ORGANISM: Artificial sequence
<220> FEATURE:
<223> OTHER INFORMATION: synthetic sequence

<400> SEQUENCE: 58
aatgtactgg ggtggttttg ggcccacccc aaaatttagc taatcg     46

<210> SEQ ID NO 59
<211> LENGTH: 45
<212> TYPE: DNA
<213> ORGANISM: Artificial sequence
<220> FEATURE:
<223> OTHER INFORMATION: synthetic sequence

<400> SEQUENCE: 59
agtcaaattt tccgtgatag ttaacagtgg acaagtcaac ctatt     45

<210> SEQ ID NO 60
<211> LENGTH: 1739
<212> TYPE: DNA
<213> ORGANISM: Artificial sequence
<220> FEATURE:
<223> OTHER INFORMATION: synthetic sequence

<400> SEQUENCE: 60

| | |
|---|---|
| atggattgca taaagaagat gtggtcagtc gtgaagaaat ttaggaagga agaagaagat | 60 |
| gtagcaaatc tgttcctgca aaatggaggt gcgctgttgg aagagcttat ttctttttct | 120 |
| agtggaacat atgacattcc aatccctagt tacagtgctc aacaacttgt taacgcaaca | 180 |
| aacaacttct ctggacgtgt ccatgctagc acctacggtt acatctgtag aggaactctg | 240 |
| caaggccact ctatcttcgt caaaatgttc ataaatattc caggtaacca accatgtggg | 300 |
| ttctcaaatt aattcataat tttatttatg cttgttttta gcttacatat atatggttca | 360 |
| caaagtagtg gcagcatgta ctgttagtgt ttgtccagat tttcgtatca taattgattt | 420 |
| tcctatctcg tgaagaaaag gataatatat ttaccataat tgagtttcct ttttatatgt | 480 |
| agaagaaaat tataaatctt ccatatttgg cgagtcccct tcttgctgg aaaaagtttg | 540 |
| aaattctata aattgaagat tcgttgcttc ccattcaaca gtatccacaa tgtagccata | 600 |
| agagatttga gagtcatggt tagaggagaa ctttatgggt caagggttag tgtaccagtt | 660 |
| gtgtttgcct cttcgtgagg ttgttctttc gatattttat actctttttt atatagttga | 720 |
| ttgctcatct ctgccataga tatatagatt aattgaccga atcacgttaa tagtatctct | 780 |
| tttggtagat ttcacttttg ttgtctgatt tatcgtcgct aaaggtttgc tttactagct | 840 |
| tccgcatgat acctaattat ttcggtcata acagaaacac agttatattg aattaaaatc | 900 |
| ttggatccac ctttgcaggt aaccttgcct cacattccga atttgacatt cttgctggag | 960 |
| ctgtacgtga catttcaatc acatctctaa tgagcggaaa taagaatgtt ttaaagatta | 1020 |
| taggttgttg tttggaattc agatatccag cgcttgtata cgaggacgcg cgattcgaaa | 1080 |
| ccctcgcaaa cttctctgat ccgaactgtg acaagttact ttcctggaag tgcaggctta | 1140 |
| aaatcgctaa gtccatcgct agcgcgatac tttacctgca taccgccttc cccacgccta | 1200 |
| tcatttatag gattttgaat cctcacaata taattctcga tcaccactgt gtaccaaagt | 1260 |
| tattcgactt tagtttcgtc ataagtttgc cgccagggga actcaaggtt gaggacgatc | 1320 |
| ttatctggat accaggatac ttcgatccag agtaccaatc ttcaaggttt gtcactcaaa | 1380 |
| agaccgacgt ctatagtttt ggtgtgctgc tactggtgct cttaaatgga cagggtccta | 1440 |
| tatgcagggc caatgaagat gatccagaac acattgtgaa ttatgtaaat gaccatattc | 1500 |
| acaaggatga tcaattcaag cacattgtgg accctaaaat cttgaacgaa tcgagtgtaa | 1560 |
| atcatcaaca gctacaagct ttcattgata tcgctttaag atgtgtccag gctaagggag | 1620 |
| aaaatagacc agatatgttc gagattgcaa gaaagatcct gcaatttgag gattataagg | 1680 |
| accatgacgg agactataag gaccatgacc tcgattataa ggacgatgac gataagtag | 1739 |

<210> SEQ ID NO 61
<211> LENGTH: 54
<212> TYPE: PRT
<213> ORGANISM: Bougainvillea spectabilis

<400> SEQUENCE: 61

Glu Leu Pro Ser Tyr Leu Lys Ser Cys Phe Leu Ala Leu Ser Ile Tyr
1               5                   10                  15

Pro Glu Asp Cys Val Ile Ser Lys Asp Gln Leu Val Arg Trp Trp Ile
            20                  25                  30

Gly Glu Gly Phe Val Pro Val Arg Arg Leu Ser Thr Glu Ala Ser Glu
        35                  40                  45

Asp Cys Phe Ser Gly Leu
    50

<210> SEQ ID NO 62
<211> LENGTH: 56
<212> TYPE: PRT
<213> ORGANISM: Boerhavia coccinea

<400> SEQUENCE: 62

Glu Leu Pro Ser Tyr Leu Lys Ser Cys Phe Leu Ser Leu Ser Ile Tyr
1               5                   10                  15

Pro Glu Asp Cys Val Ile Ser Lys Asp Gln Leu Val Arg Trp Trp Ile
            20                  25                  30

Gly Glu Gly Phe Val Pro Val Arg Asn Gly Arg Leu Ser Thr Glu Ala
        35                  40                  45

Ser Glu Asp Cys Phe Ser Gly Leu
    50                  55

<210> SEQ ID NO 63
<211> LENGTH: 56
<212> TYPE: PRT
<213> ORGANISM: Synsepalum dulcificum

<400> SEQUENCE: 63

Glu Leu Pro Pro Tyr Leu Lys Leu Cys Phe Leu Cys Phe Ser Leu Tyr
1               5                   10                  15

Pro Glu Asp Ile Glu Ile Glu Arg Lys Gln Leu Ile His Trp Trp Ile
            20                  25                  30

Gly Glu Gly Phe Ile Leu Leu Arg Asn Gly Arg Leu Pro Thr Glu Gly
        35                  40                  45

Gly Glu Tyr Cys Phe Ser Glu Leu
    50                  55

<210> SEQ ID NO 64
<211> LENGTH: 56
<212> TYPE: PRT
<213> ORGANISM: Manilkara zapota

<400> SEQUENCE: 64

Glu Leu Pro Pro Tyr Leu Lys Ser Cys Phe Leu Cys Phe Ser Leu Tyr
1               5                   10                  15

Pro Glu Asp Ile Glu Ile Glu Arg Asn Gln Leu Ile His Trp Trp Ile
            20                  25                  30

Gly Glu Gly Phe Ile Leu Leu Arg Asn Gly Arg Leu Ser Thr Glu Ala
        35                  40                  45

Gly Glu Tyr Cys Phe Ser Glu Leu
    50                  55

<210> SEQ ID NO 65
<211> LENGTH: 56
<212> TYPE: PRT
<213> ORGANISM: Ardisia humilis

<400> SEQUENCE: 65

Glu Leu Pro Pro Tyr Leu Lys Ser Cys Phe Leu Cys Phe Ser Leu Tyr

```
                1               5                  10                  15
        Pro Glu Asp Cys Val Ile Glu Lys Ala Gln Leu Ile Arg Trp Trp Ile
                        20                  25                  30

Gly Glu Gly Phe Ile Pro Met Arg Asn Gly Arg Pro Ser Thr Gln Ala
                    35                  40                  45

Gly Glu Tyr Cys Phe Ser Glu Leu
                50                  55

<210> SEQ ID NO 66
<211> LENGTH: 56
<212> TYPE: PRT
<213> ORGANISM: Mertensia paniculata

<400> SEQUENCE: 66

Glu Leu Pro Pro Tyr Leu Lys Ser Cys Leu Leu Cys Leu Ser Leu Phe
        1               5                  10                  15

Pro Glu Asp Cys Val Ile Ala Lys Glu Gln Leu Ile Ser Trp Trp Ile
                        20                  25                  30

Gly Glu Ser Phe Ile Pro Leu Arg Asn Thr Arg Leu Ser Thr Glu Ile
                    35                  40                  45

Gly Glu Asp Cys Phe Ser Glu Leu
                50                  55

<210> SEQ ID NO 67
<211> LENGTH: 56
<212> TYPE: PRT
<213> ORGANISM: Phacelia campanularia

<400> SEQUENCE: 67

Glu Leu Pro Pro Phe Leu Lys Ser Cys Phe Leu Cys Phe Ser Leu Phe
        1               5                  10                  15

Pro Glu Asp Cys Val Ile Pro Lys Glu Gln Val Ile Asn Trp Trp Ile
                        20                  25                  30

Gly Glu Ser Phe Val Pro Leu Arg Asn Ser Arg Leu Leu Thr Glu Val
                    35                  40                  45

Gly Glu Asp Cys Phe Ser Glu Leu
                50                  55

<210> SEQ ID NO 68
<211> LENGTH: 56
<212> TYPE: PRT
<213> ORGANISM: Heliotropium mendocinum

<400> SEQUENCE: 68

Glu Leu Pro Lys Phe Leu Lys Ser Cys Phe Leu Cys Phe Ser Leu Phe
        1               5                  10                  15

Pro Glu Asp Arg Val Ile Pro Lys Glu Gln Leu Ile Asn Trp Trp Ile
                        20                  25                  30

Gly Glu Ser Phe Val Pro Leu Arg Asn Gly Arg Leu Leu Ile Glu Val
                    35                  40                  45

Gly Glu Asp Cys Phe Thr Glu Leu
                50                  55

<210> SEQ ID NO 69
<211> LENGTH: 56
<212> TYPE: PRT
<213> ORGANISM: Ligustrum sinense

<400> SEQUENCE: 69
```

```
Glu Leu Ser Pro Tyr Leu Lys Ser Cys Phe Leu Cys Phe Ser Leu Phe
1               5                   10                  15

Pro Glu Asp Cys Glu Ile Ala Lys Asp Gln Leu Ile His Trp Trp Ile
            20                  25                  30

Ala Glu Asn Phe Ile Pro Leu Arg Thr Gly Leu Leu Ser Thr Glu Val
        35                  40                  45

Ala Glu Asn Cys Phe Ser Glu Leu
    50                  55

<210> SEQ ID NO 70
<211> LENGTH: 56
<212> TYPE: PRT
<213> ORGANISM: Nicotiana tabacum

<400> SEQUENCE: 70

Glu Leu Pro Pro Tyr Leu Lys Ser Cys Phe Leu Cys Phe Ser Leu Phe
1               5                   10                  15

Pro Glu Asp Cys Val Ile Pro Lys Asp Gln Leu Ile Arg Trp Trp Ile
            20                  25                  30

Gly Glu Ser Phe Ile Pro Leu Arg Ser Gly Arg Leu Ser Thr Glu Val
        35                  40                  45

Gly Glu Asp Cys Phe Ser Gln Leu
    50                  55

<210> SEQ ID NO 71
<211> LENGTH: 56
<212> TYPE: PRT
<213> ORGANISM: Nicotiana sylvestris

<400> SEQUENCE: 71

Glu Leu Pro Pro Tyr Leu Lys Ser Cys Phe Leu Cys Phe Ser Leu Phe
1               5                   10                  15

Pro Glu Asp Cys Val Ile Pro Lys Asp Gln Leu Ile Arg Trp Trp Ile
            20                  25                  30

Gly Glu Ser Phe Ile Pro Leu Arg Ser Gly Arg Ser Ser Thr Glu Val
        35                  40                  45

Gly Glu Asp Cys Phe Ser Gln Leu
    50                  55

<210> SEQ ID NO 72
<211> LENGTH: 56
<212> TYPE: PRT
<213> ORGANISM: Nicotiana attenuata

<400> SEQUENCE: 72

Glu Leu Pro Pro Tyr Leu Lys Ser Cys Phe Leu Cys Phe Ser Leu Phe
1               5                   10                  15

Pro Glu Asp Cys Val Ile Pro Lys Asp Gln Leu Ile Arg Trp Trp Ile
            20                  25                  30

Gly Glu Ser Phe Ile Pro Leu Arg Ser Gly Arg Leu Ser Thr Glu Val
        35                  40                  45

Gly Glu Asp Cys Phe Ser Gln Leu
    50                  55

<210> SEQ ID NO 73
<211> LENGTH: 56
<212> TYPE: PRT
<213> ORGANISM: Unknown
<220> FEATURE:
<223> OTHER INFORMATION: NbZAR1
```

```
<400> SEQUENCE: 73

Glu Leu Pro Pro Tyr Leu Lys Ser Cys Phe Leu Cys Phe Ser Leu Phe
1               5                   10                  15

Pro Glu Asp Cys Val Ile Pro Lys Asp Gln Leu Ile Arg Trp Trp Ile
            20                  25                  30

Gly Glu Gly Phe Ile Pro Leu Arg Ser Gly Arg Leu Ser Thr Glu Val
        35                  40                  45

Gly Glu Asp Cys Phe Ser Gln Leu
    50                  55

<210> SEQ ID NO 74
<211> LENGTH: 56
<212> TYPE: PRT
<213> ORGANISM: Capsicum annuum

<400> SEQUENCE: 74

Glu Leu Pro Pro Tyr Leu Lys Ser Cys Phe Leu Cys Phe Ser Leu Phe
1               5                   10                  15

Pro Glu Asp Cys Val Ile Pro Lys Asp Gln Leu Ile Arg Trp Trp Ile
            20                  25                  30

Gly Glu Ser Phe Ile Pro Leu Arg Ser Gly Arg Leu Ser Thr Glu Val
        35                  40                  45

Gly Glu Asp Cys Phe Ser Gln Leu
    50                  55

<210> SEQ ID NO 75
<211> LENGTH: 56
<212> TYPE: PRT
<213> ORGANISM: Solanum ptycanthum

<400> SEQUENCE: 75

Glu Leu Pro Pro Tyr Leu Lys Ser Cys Phe Ile Cys Phe Ser Leu Phe
1               5                   10                  15

Pro Glu Asp Cys Val Ile Pro Lys Asp Gln Leu Ile Arg Trp Trp Ile
            20                  25                  30

Gly Glu Ser Phe Ile Pro Leu Arg Ser Gly Arg Leu Ser Thr Glu Val
        35                  40                  45

Gly Glu Asp Cys Phe Ser Gln Leu
    50                  55

<210> SEQ ID NO 76
<211> LENGTH: 56
<212> TYPE: PRT
<213> ORGANISM: Solanum tuberosum

<400> SEQUENCE: 76

Glu Leu Pro Pro Tyr Leu Lys Ser Cys Phe Leu Cys Phe Ser Leu Phe
1               5                   10                  15

Pro Glu Asp Cys Val Ile Leu Lys Asp Gln Leu Ile Arg Trp Trp Ile
            20                  25                  30

Gly Glu Ser Phe Ile Pro Leu Arg Ser Gly Arg Leu Ser Thr Glu Val
        35                  40                  45

Gly Glu Asp Cys Phe Ser Gln Leu
    50                  55

<210> SEQ ID NO 77
<211> LENGTH: 56
<212> TYPE: PRT
```

-continued

<213> ORGANISM: Unknown
<220> FEATURE:
<223> OTHER INFORMATION: Slzar1

<400> SEQUENCE: 77

Glu Leu Pro Pro Tyr Leu Lys Ser Cys Phe Leu Cys Phe Ser Leu Phe
1               5                   10                  15

Pro Glu Asp Cys Val Ile Leu Lys Asp Lys Leu Ile Arg Trp Trp Ile
            20                  25                  30

Gly Glu Ser Phe Ile Pro Leu Arg Ser Gly Arg Leu Ser Thr Glu Val
        35                  40                  45

Gly Glu Asp Cys Phe Ser Gln Leu
    50                  55

<210> SEQ ID NO 78
<211> LENGTH: 56
<212> TYPE: PRT
<213> ORGANISM: Solanum pennellii

<400> SEQUENCE: 78

Glu Leu Pro Pro Tyr Leu Lys Ser Cys Phe Leu Cys Phe Ser Leu Phe
1               5                   10                  15

Pro Glu Asp Cys Val Ile Leu Lys Asp Gln Leu Ile Arg Trp Trp Ile
            20                  25                  30

Gly Glu Ser Phe Ile Pro Leu Arg Ser Gly Arg Leu Ser Thr Glu Val
        35                  40                  45

Gly Glu Asp Cys Phe Ser Gln Leu
    50                  55

<210> SEQ ID NO 79
<211> LENGTH: 56
<212> TYPE: PRT
<213> ORGANISM: Wrightia natalensis

<400> SEQUENCE: 79

Glu Leu Pro Pro Tyr Leu Lys Thr Cys Phe Leu Cys Phe Ala Leu Phe
1               5                   10                  15

Pro Glu Asp Cys Glu Val Asp Lys Glu Gln Leu Ile His Trp Trp Ile
            20                  25                  30

Gly Glu Ser Phe Ile Pro Val Arg Asn His Arg Leu Ser Thr Glu Val
        35                  40                  45

Gly Glu Asp Cys Phe Ser Glu Leu
    50                  55

<210> SEQ ID NO 80
<211> LENGTH: 56
<212> TYPE: PRT
<213> ORGANISM: Apocynum androsaemifolium

<400> SEQUENCE: 80

Glu Leu Pro Pro Tyr Leu Lys Thr Cys Phe Leu Cys Phe Ala Leu Phe
1               5                   10                  15

Pro Glu Asp Cys Glu Val Asp Lys Glu Gln Leu Ile His Trp Trp Ile
            20                  25                  30

Gly Glu Ser Phe Ile Pro Val Arg Asn His Arg Leu Ser Thr Glu Val
        35                  40                  45

Gly Glu Asp Cys Phe Ser Glu Leu
    50                  55

```
<210> SEQ ID NO 81
<211> LENGTH: 56
<212> TYPE: PRT
<213> ORGANISM: Coffea canephora

<400> SEQUENCE: 81

Glu Leu Pro Pro Tyr Leu Lys Ser Cys Phe Leu Cys Phe Ser Ile Phe
1               5                   10                  15

Pro Glu Asp Cys Val Val Asp Lys Asp Gln Leu Val His Trp Trp Ile
            20                  25                  30

Gly Glu Ser Phe Met Pro Val Arg Asn His Arg Leu Ser Thr Glu Val
        35                  40                  45

Gly Glu Asp Cys Phe Ser Glu Leu
    50                  55

<210> SEQ ID NO 82
<211> LENGTH: 56
<212> TYPE: PRT
<213> ORGANISM: Psychotria ipecacuanha

<400> SEQUENCE: 82

Glu Leu Pro Pro Tyr Leu Lys Thr Cys Phe Leu Cys Phe Ser Val Phe
1               5                   10                  15

Pro Glu Asp Cys Val Ile Asp Lys Glu Gln Leu Val His Trp Trp Ile
            20                  25                  30

Gly Glu Ser Phe Ile Pro Val Arg Asn His Arg Leu Ser Thr Glu Val
        35                  40                  45

Gly Glu Asp Cys Phe Ser Glu Leu
    50                  55

<210> SEQ ID NO 83
<211> LENGTH: 56
<212> TYPE: PRT
<213> ORGANISM: Centella asiatica

<400> SEQUENCE: 83

Glu Leu Pro Pro Tyr Leu Lys Ser Cys Phe Leu Cys Phe Ser Leu Tyr
1               5                   10                  15

Pro Glu Asp Cys Glu Ile Val Lys Asp Gln Val Ile Tyr Trp Trp Ile
            20                  25                  30

Gly Glu Ser Phe Ile Pro Leu Lys Asn Gly Arg Pro Ser Thr Gln Val
        35                  40                  45

Gly Glu Asp Cys Phe Ser Glu Leu
    50                  55

<210> SEQ ID NO 84
<211> LENGTH: 56
<212> TYPE: PRT
<213> ORGANISM: Hedera helix

<400> SEQUENCE: 84

Glu Leu Pro Pro Tyr Leu Lys Ser Cys Phe Leu Cys Leu Ser Leu Tyr
1               5                   10                  15

Pro Glu Asp Cys Glu Ile Ala Lys Glu Gln Leu Ile Tyr Trp Trp Ile
            20                  25                  30

Gly Glu Ser Phe Ile Pro Leu Asn Asn Gly Lys Pro Ser Thr Gln Val
        35                  40                  45

Gly Glu Asp Cys Phe Ser Glu Leu
    50                  55
```

```
<210> SEQ ID NO 85
<211> LENGTH: 56
<212> TYPE: PRT
<213> ORGANISM: Exocarpos cupressiformis

<400> SEQUENCE: 85

Glu Leu Pro Ser Tyr Leu Lys Ser Cys Phe Cys Leu Ser Leu Tyr
1               5                   10                  15

Pro Glu Asp Cys Val Ile Pro Lys Glu Gln Leu Val Tyr Trp Trp Ile
            20                  25                  30

Gly Glu Gly Phe Val Pro Leu Arg His Gly Arg Met Trp Ile Glu Ser
        35                  40                  45

Gly Glu Asp Cys Phe Thr Gly Leu
    50                  55

<210> SEQ ID NO 86
<211> LENGTH: 56
<212> TYPE: PRT
<213> ORGANISM: Hakea prostrata

<400> SEQUENCE: 86

Glu Leu Pro Ser Asn Leu Lys Ser Cys Leu Cys Phe Ser Leu Tyr
1               5                   10                  15

Pro Glu Asp Cys Val Ile Thr Lys Lys Gln Leu Val Asn Trp Trp Ile
            20                  25                  30

Gly Glu Gly Phe Val Pro Met Thr Ser Gly Leu Thr Thr Leu Ala
        35                  40                  45

Ala Glu Asp Cys Phe Ser Gly Leu
    50                  55

<210> SEQ ID NO 87
<211> LENGTH: 56
<212> TYPE: PRT
<213> ORGANISM: Annona muricata

<400> SEQUENCE: 87

Glu Leu Pro Ala His Leu Lys Ala Cys Phe Leu Ser Leu Ser Ile Tyr
1               5                   10                  15

Pro Glu Asp Cys Ala Ile Val Lys Glu Gln Leu Ile His Trp Trp Met
            20                  25                  30

Gly Glu Gly Phe Val Pro Met Arg Asn Gly His Leu Thr Ile Asp Met
        35                  40                  45

Gly Glu Ala Cys Phe Ser Gly Leu
    50                  55

<210> SEQ ID NO 88
<211> LENGTH: 56
<212> TYPE: PRT
<213> ORGANISM: Eupomatia bennettii

<400> SEQUENCE: 88

Glu Leu Pro Ala His Leu Lys Ser Cys Leu Leu Ser Phe Ser Ile Tyr
1               5                   10                  15

Pro Glu Asp Ser Val Ile Leu Lys Glu Gln Val Ile His Trp Trp Ile
            20                  25                  30

Gly Glu Gly Phe Val Pro Met Arg Asn Gly His Leu Thr Ile Glu Leu
        35                  40                  45

Gly Glu Ala Cys Phe Ser Gly Leu
    50                  55
```

<210> SEQ ID NO 89
<211> LENGTH: 56
<212> TYPE: PRT
<213> ORGANISM: Hibbertia grossulariifolia

<400> SEQUENCE: 89

Glu Leu Pro Ser His Leu Lys Pro Cys Phe Leu Ser Phe Ser Leu Tyr
1               5                   10                  15

Pro Glu Asp Cys Glu Ile Pro Lys Glu Gln Leu Thr Tyr Trp Trp Ile
            20                  25                  30

Ala Glu Gly Phe Ile Pro Arg Arg Gly Arg Leu Ile Val Glu Ser
        35                  40                  45

Ser Glu Asp Cys Phe Ser Gly Leu
    50                  55

<210> SEQ ID NO 90
<211> LENGTH: 56
<212> TYPE: PRT
<213> ORGANISM: Ludovia sp.

<400> SEQUENCE: 90

Glu Leu Pro Ser His Leu Lys Pro Cys Phe Leu Cys Leu Ser Ile Tyr
1               5                   10                  15

Pro Glu Asp Cys Ile Ile Thr Lys Asp Gln Leu Val Arg Trp Trp Ile
            20                  25                  30

Ala Glu Gly Phe Val Pro Arg His Gly Gly Arg Ser Leu Val Glu Ser
        35                  40                  45

Gly Glu Glu Cys Phe Ala Gly Leu
    50                  55

<210> SEQ ID NO 91
<211> LENGTH: 56
<212> TYPE: PRT
<213> ORGANISM: Anthurium amnicola

<400> SEQUENCE: 91

Glu Leu Pro Thr Tyr Leu Lys Pro Cys Leu Leu Cys Phe Ala Val Tyr
1               5                   10                  15

Pro Glu Asp Cys Val Ile Leu Lys Asp Gln Leu Ile His Trp Trp Ile
            20                  25                  30

Gly Glu Gly Phe Val Pro Ala Lys Ser Asp Gly Leu Leu Ile Glu Trp
        35                  40                  45

Gly Glu Asp Cys Phe Met Gly Leu
    50                  55

<210> SEQ ID NO 92
<211> LENGTH: 56
<212> TYPE: PRT
<213> ORGANISM: Pistia stratioites

<400> SEQUENCE: 92

Glu Leu Pro Thr Tyr Leu Lys Ser Cys Phe Leu Cys Phe Val Val Tyr
1               5                   10                  15

Pro Glu Asp Cys Val Val Ile Lys Asp Gln Leu Ile His Trp Trp Met
            20                  25                  30

```
Gly Glu Gly Phe Leu Pro Ala Ser Ser Gly Arg Ser Leu Val Glu Ile
        35                  40                  45

Gly Glu Asp Cys Phe Thr Gly Leu
        50                  55
```

ZAR1 AND JIM2 MEDIATE RESISTANCE AGAINST PLANT PATHOGENS CONTAINING YOPJ-FAMILY EFFECTORS

CROSS-REFERENCE TO RELATED APPLICATIONS

This application is the national phase under 35 U.S.C. § 371 of International Application No. PCT/US2019/033962, filed on May 24, 2019, which claims the benefit of U.S. provisional application Ser. No. 62/692,537, filed on Jun. 29, 2018, which applications are incorporated by reference in their entirety.

STATEMENT REGARDING FEDERALLY SPONSORED RESEARCH

This invention was made with government support under Grant Number 2016-67012-25106 awarded by the United States Department Of Agriculture. The government has certain rights in the invention.

BACKGROUND

Bacterial phytopathogens in the genus *Xanthomonas* use a Type III Secretion System to deliver effector proteins into the plant cell. Effector proteins can function to inhibit plant immunity or manipulate the metabolism of the host to favor growth of the bacteria (Gürlebeck et al., 2006). If the plant is able to detect the presence of an effector protein, a strong immune response may be induced which prevents pathogen proliferation and restricts host range (Alfano and Collmer, 2004; Castañeda et al., 2005; Wei et al., 2007; Schwartz et al., 2015). This strong immune response often results in localized cell death known as the hypersensitive response. Identifying the pathway responsible for mediating effector protein recognition can enable efforts to engineer disease resistance in susceptible crop species (Wulff et al., 2011).

The perception of intracellular pathogen effector proteins in plants is frequently mediated by proteins from a large gene family known as the Nucleotide binding, Leucine-rich Repeat (NLR) proteins (Jones et al., 2016). NLR recognition of an effector protein can occur through a physical interaction between the NLR and the cognate effector or by an indirect mechanism in which the NLR protein is "guarding" another component which is modified by the effector (Khan et al., 2016). While plants have additional receptor pathways independent from the NLRs, such as Receptor-Like Kinases (Macho and Zipfel, 2014), NLR proteins have been demonstrated to mediate many resistance responses against a broad range of pathogens including bacteria, fungi, oomycetes, viruses and nematodes (Dodds and Rathjen, 2010).

Tomato is susceptible to *Xanthomonas perforans* which causes the disease Bacterial Leaf Spot. This disease can result in significant yield losses in commercial tomato production and there is limited genetic resistance available within commercial cultivars (Stall et al., 2009; Kim et al., 2015). The plant *Nicotiana benthamiana* is resistant to *X. perforans* due to the presence of several pathways capable of perceiving effector proteins found in this pathogen including AvrBsT, XopQ and XopJ4/AvrXv4 (Roden et al., 2004; Schwartz et al., 2015). The XopJ4 effector is widely conserved among strains of *X. perforans* and has therefore been proposed as a good target for genetic mechanisms of disease resistance against this pathogen (Timilsina et al., 2016).

XopJ4 is part of the YopJ family of effector proteins. These effectors are distributed across many species of bacterial pathogens of both plants and animals and are thought to be acetyltransferases that disrupt the function of proteins inside the host cell (Ma and Ma, 2016). The YopJ effector protein HopZ1a from *Pseudomonas syringae* is recognized in *Arabidopsis thaliana* and triggers a hypersensitive cell death response (HR) that depends on the NLR protein ZAR1 and the Receptor-Like Cytoplasmic Kinase (RLCK) family XII protein ZED1 (Lewis et al., 2010; Lewis et al., 2013). HopZ1a has been reported to directly acetylate ZED1, which interacts with ZAR1 to initiate an immune response. ZAR1 is also required for the perception of several non-YopJ effectors in *Arabidopsis* including the *Xanthomonas* AvrAC (Wang et al., 2015) and the *Pseudomonas syringae* HopF2a (Seto et al., 2017). In each case, a different RLCK XII family member is required for the immune response and for AvrAC an additional RLCK VII protein is also required.

The YopJ effector PopP2 from *Ralstonia solanacearum* is recognized in *Arabidopsis thaliana* by a ZAR1-independent pathway (Deslandes et al., 2002). PopP2 acetylates a WRKY domain on the NLR protein RRS1 to trigger immune activation (Sarris et al., 2015). The NLR protein RPS4 is required for RRS1-mediated perception of PopP2 and is thought to form a complex with RRS1 (Narusaka et al., 2009; Williams et al., 2014). The widespread distribution of YopJ-family effector proteins and the existence of two evolutionarily independent mechanisms for the perception of YopJ effectors highlights the importance of these proteins in pathogenesis.

Four YopJ effector proteins have been identified in various *Xanthomonas* species, although not all *Xanthomonas* have YopJ effectors. These include XopJ4/AvrRx4, XopJ, AvrRxv and AvrBsT. AvrRxv, XopJ4 and AvrBsT have all been associated with avirulence responses in various Solanaceous plant species, although the recognition mechanisms for the perception of these effectors are not well understood (Minsavage et al., 1990; Whalen et al., 1993; Astua-Monge et al., 2000). The AvrBsT effector triggers a strong avirulence response on pepper and *N. benthamiana*. The recognition of AvrBsT in pepper has been reported to be dependent on SGT1 and PIK1 (Kim et al., 2014). AvrRxv triggers an avirulence response on tomato line Hawaii 7998, the basis for which is multi-genic based on segregation analysis (Whalen et al., 1993; Yu et al., 1995). XopJ4 triggers an avirulence response on *Solanum pennellii* accession LA716. While efforts have been made to map the resistance genes for AvrRxv and XopJ4 (Yu et al., 1995; Astua-Monge et al., 2000; Sharlach et al., 2013), the genes involved have not been conclusively identified.

SUMMARY

Provided herein is a plant comprising an exogenous polynucleotide encoding a JIM2 polypeptide, where the exogenous polynucleotide is operably linked to a promoter and the plant expresses the JIM2 polypeptide. In some embodiments, the plants have enhanced resistance to at least one species of *Xanthomonas*.

These and other inventions are described in greater detail below.

BRIEF DESCRIPTION OF THE DRAWINGS

The skilled artisan will understand that the drawings, described below, are for illustration purposes only. The drawings are not intended to limit the scope of the present teachings in any way.

FIG. 9. SpJIM2 functions in XopJ4 perception. A homolog of JIM2 from *Solanum pennellii* (SpJIM2) was cloned and transiently expressed in a line of *N. benthamiana* deficient for NbJIM2 using *Agrobacterium*. Co-expression of XopJ4 and SpJIM2 resulted in a strong immune response at three days post infiltration. The data in this figure shows that the *Solanum pennellii* JIM2 gene can mediate perception of XopJ4 despite having significant sequence divergence from NbJIM2.

FIG. 12. Sequence of the codon-altered, VIGS-resistant JIM2 construct. The VIGS construct was designed to target part of the $2^{nd}$ exon of JIM2. To design a VIGS-resistant version of JIM2, the codon usage was altered so that the VIGS cassette would have limited identity with the nucleotide sequence but the predicted amino acid sequence would not be affected. The sequence is set forth in SEQ ID NO: 60.

DEFINITIONS

Figure 1:
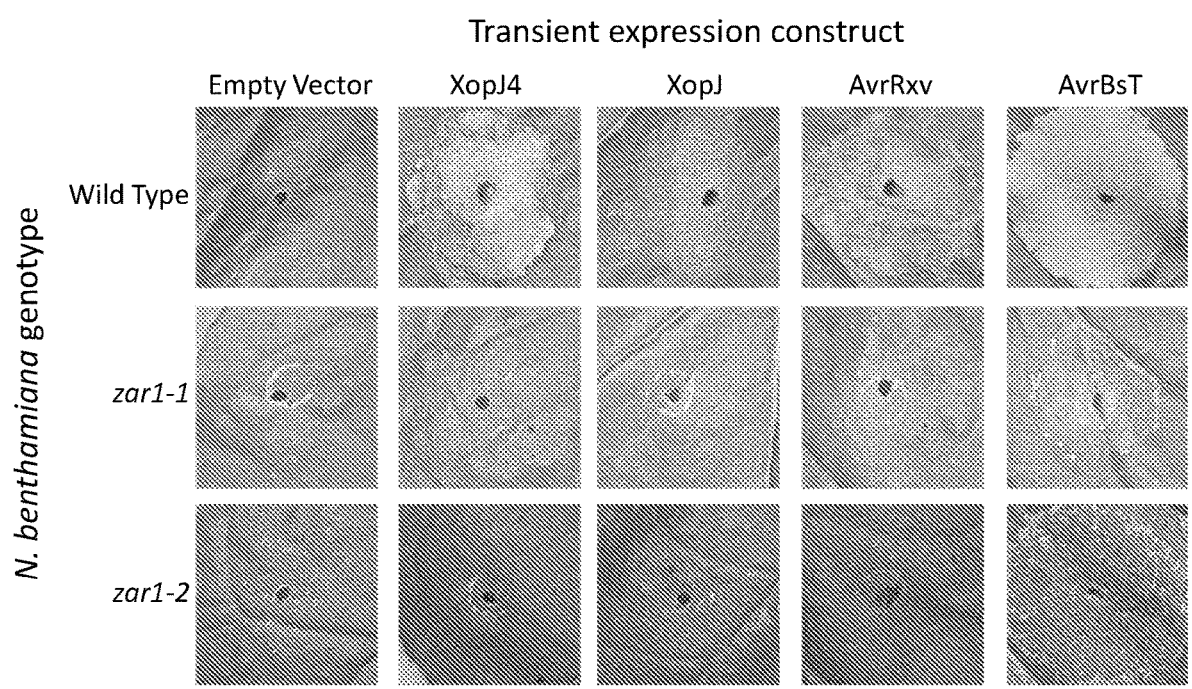
FIG. 1. Response to *Xanthomonas* YopJ effectors in the zar1 mutants. The indicated YopJ effectors were transiently expressed in wild type or the mutant *N. benthamiana* plants using *Agrobacterium* infiltrated at an $OD_{600}$ of 0.5. The plants were imaged three days post infiltration. XopJ4 and AvrBsT are from *X. perforans* 4B whereas XopJ and AvrRxv are from *X. euvesicatoria* 85-10. The data shown in this figure indicates that the NbZAR1 is required for perception of XopJ4, XopJ and AvrRxv in *N. benthamiana*. The visible cell death response to AvrBsT is weaker but still present in the zar1 mutant plants, indicating that NbZAR1 mediates perception of AvrBsT but there is also an NbZAR1-independent pathway for perception of this effector.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

As used herein, "resistance" is a relative term in that the presence of a polypeptide of the invention (i) reduces the disease symptoms of a plant comprising the gene (R (resistant) gene) that confers resistance, relative to a plant lacking the R gene, and/or (ii) reduces pathogen reproduction or spread on a plant or within a population of plants comprising the R gene. Resistance as used herein is relative to the "susceptible" response of a plant to the same pathogen. Typically, the presence of the R gene improves at least one production trait of a plant comprising the R gene when infected with the pathogen, such as grain yield, when compared to an isogenic plant infected with the pathogen but lacking the R gene. The isogenic plant may have some level of resistance to the pathogen, or may be classified as susceptible. Thus, the terms "resistance" and "enhanced resistance" are generally used herein interchangeably. Furthermore, a polypeptide of the invention does not necessarily confer complete pathogen resistance, for example when some symptoms still occur or there is some pathogen reproduction on infection but at a reduced amount within a plant or a population of plants. Resistance may occur at only some stages of growth of the plant, for example in adult plants (fully grown in size) and less so, or not at all, in seedlings, or at all stages of plant growth. By using a transgenic strategy to express an polypeptide in a plant, the plant of the invention can be provided with resistance. Enhanced resistance can be determined by a number of methods known in the art such as analysing the plants for the amount of pathogen and/or analysing plant growth or the amount of damage or disease symptoms to a plant in the presence of the pathogen, and comparing one or more of these parameters to an isogenic plant lacking an exogenous gene encoding a polypeptide of the invention.

The term "exogenous" means that the sequence of the polynucleotide is not found in the wild type species of plant in which it is present. A plant that contains an exogenous polynucleotide has a genome that has been modified to contain the polynucleotide. The polynucleotide may be from another plant or it may have a nucleotide sequence that encodes a polypeptide from another plant. An exogenous polynucleotide may encode a variant of a polypeptide from another plant (e.g., a polypeptide that is at least 95% identical to a reference polypeptide). For example, a tomato plant that contains an exogenous polynucleotide has a genome that has been modified to contain a polynucleotide that is not from tomato. An "exogenous" nucleic acid can be introduced into a genome of a cell via a number of different methods. For example, in some cases the plant may be transgenic, in which case the exogenous nucleic acid may be introduced from the outside (e.g., by introducing a coding sequence into the plant). In other cases, an exogenous nucleic acid can be introduced by modifying a sequence that already exists in the genome by genome editing. In other cases, the plant may be cisgenic, in which case the exogenous nucleic acid may be introduced into by plant breeding, i.e., by introgressing a gene from another species into the plant.

Reference to a particular protein, e.g., JIM2, includes wild type proteins from other plant species as well as variants of those proteins that do not have a wild type sequence but are at least 80%, e.g., at least 85%, at least 90% or at least 95% identical to a wild type sequence and remain functional.

Other definitions of terms may appear throughout the specification.

DETAILED DESCRIPTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a nucleic acid" includes a plurality of such nucleic acids and reference to "the compound" includes reference to one or more compounds and equivalents thereof known to those skilled in the art, and so forth.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, A., *Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

A plant comprising an exogenous polynucleotide encoding a JIM2 polypeptide is provided. In some embodiments, the plant may comprise an exogenous polynucleotide encoding a ZAR1 polypeptide. The plant may have enhanced resistance to bacterial pathogens that contain a YopJ effector. For example, the plant may have enhanced resistance to at least one species of *Xanthomonas* (e.g., *Xanthomonas perforans*) relative to a control plant that is otherwise identical to the plant but does not contain the exogenous polynucleotide. In these embodiments, the plant should not have an endogenous functional JIM2 gene, i.e., a JIM2 gene that is native to the plant and mediates recognition of XopJ4 or a related YopJ effector protein.

In some embodiments, the JIM2 polypeptide may be at least 80% identical (e.g., at least 85%, at least 90%, at least 95%, at least 98%, at least 99% identical, or 100% identical to) to the *Nicotiana benthamiana* JIM2 (SEQ ID NO: 1) or *Solanum pennellii* JIM2 (SEQ ID NO: 2). The amino acid sequences of these proteins are shown below:

```
Nicotiana benthamiana JIM2 (SEQ ID NO: 1):
MDCIKKMWSVVKKFRKEEEDVANLFLQNGGALLEELISFSSGTYDIPIPS

YSAQQLVNATNNFSGRVHASTYGYICRGTLQGHSIFVKMFINIPGNLASH

SEFDILAGAVRDISITSLMSGNKNVLKIIGCCLEFRYPALVYEDARFETL

ANFLDPNCDKLLSWKCRLKIAKSIASAILYLHTAFPTPIIYRILNPHNII

LDHHCVPKLFDFSFVISLPPGELKVEDDLIWIPGYFDPEYQSSRFVTQKT

DVYSFGVLLLVLLNGOGPICRANEDDPEHIVNYVNDHIHKDDQFKHIVDP

KILNESSVNHQQLQAFIDIALRCVQAKGENRPDMFEIARKILQFE

Solanum pennellii JIM2 (SEQ ID NO: 2):
MQFFRELTIRKKQSLSEEWRKKEHDYYLHNGSAVLEELLALCNGNCRIPI

RYFTASEIDDAISYSQNELEIFDGRMVAGSMDKRLVFVRFFPNYFRNFFN

IFRDIAITAQMSHLKNVLRLVGCCVEFEKPVMVYEYVEAISLHTLLFEKG

NHDDQTRKSLLSWGNRLRIANEVASAVVFLHTEFTTPIIYKDLKPSNVII

DQNSGVAKLLNFSLSVSLPPGELQVIKDVTCGTYGYLAPEYAVSGIVTQN

TDVYSFGVVLLQLLTGKNMGTLDIKDRKYIMYDVESDLDPIDIEKIYVMD

IADKAILEEYGIEIQQQLEDCWDLVKKCTKSKGEERPYMIEVAKELRRIY

NCFRVLTLGQNQLHK
```

Figure 8:
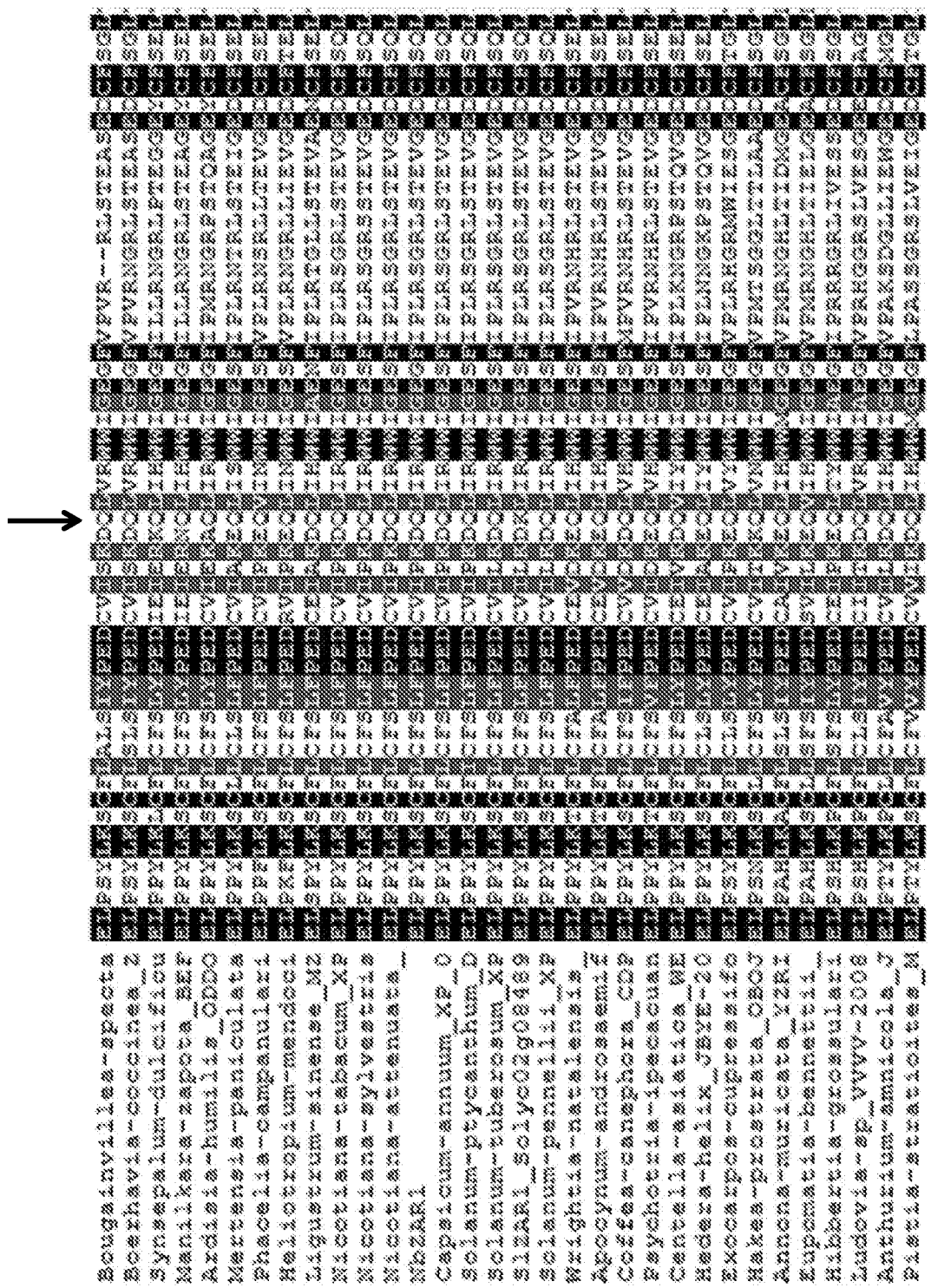
FIG. 8. Multiple protein align for SlZAR1. Putative orthologs of ZAR1 were identified by BLAST search of the NCBI and 1KP databases. A multiple sequence alignment was performed using ClustalO of the protein sequences, a subset of which is shown. The ZAR1 protein from *Solanum lycopersicum* contains several missense mutations at conserved locations including Q430K indicated above. This figure identifies a mutation in SlZAR1 at a highly conserved position which may explain why SlZAR1 is unable to complement the Nb zar1 mutant. The sequences are set forth as follows: *Bougainvillea spectabilis* (SEQ ID NO:61); *Boerhavia coccinea* (SEQ ID NO: 62); *Synsepalum dulcificum* (SEQ ID NO: 63); *Manilkara zapota* (SEQ ID NO: 64); *Ardisia humilis* (SEQ ID NO: 65); *Mertensia paniculate* (SEQ ID NO: 66); *Phacelia campanularia* (SEQ ID NO: 67); *Heliotropium mendocinum* (SEQ ID NO: 68); *Ligustrum sinense* (SEQ ID NO: 69); *Nicotiana tabacum* (SEQ ID NO: 70); *Nicotiana sylvestris* (SEQ ID NO: 71); *Nicotiana attenuate* (SEQ ID NO: 72); NbZAR1 (SEQ ID NO: 73); *Capsicum annuum* (SEQ ID NO: 74); *Solanum ptycanthum* (SEQ ID NO: 75); *Solanum tuberosum* (SEQ ID NO: 76); SlZAR1 (SEQ ID NO: 77); *Solanum pennellii* (SEQ ID NO: 78); *Wrightia natalensis* (SEQ ID NO: 79); *Apocynum androsaemifolium* (SEQ ID NO: 80); *Coffea canephora* (SEQ ID NO: 81); *Psychotria ipecacuanha* (SEQ ID NO: 82); *Centella asiatica* (SEQ ID NO: 83); *Hedera helix* (SEQ ID NO: 84); *Exocarpos cupressiformis* (SEQ ID NO: 85); *Hakea prostrata* (SEQ ID NO: 86); *Annona muricate* (SEQ ID NO: 87); *Eupomatia bennettii* (SEQ ID NO: 88); *Hibbertia grossulariifolia* (SEQ ID NO: 89); *Ludovia* sp. (SEQ ID NO: 90); *Anthurium amnicola* (SEQ ID NO: 91); *Pistia stratiotes* (SEQ ID NO: 92).

In some embodiments, the ZAR1 polypeptide may be at least 80% (e.g. at least 85%, at least 90%, at least 95%, at least 98% or 100%) identical to the *Nicotiana benthamiana* ZAR1 polypeptide (SEQ ID NO: 3). Examples of partial sequences from several ZAR1 polypeptides are shown in FIG. 8. The amino acid sequence of the *Nicotiana benthamiana* ZAR1 polypeptide is shown below:

```
Nicotiana benthamiana ZAR1 (SEQ ID NO: 3):
MVDAVVTVFLEKLLHVLTEESRFLTKYRQQFEKLKNELLFMQSFLKDAER

LKRKNNTLKGVMSCLRDLIFEAEEILEDCQNQSADSDRATTCFHPKRLSL

RHQTGKCLAKINDRISEIKQNISTYLGVPLLEEGSMEAHNNLMSRWTSSL

YDHTQVVGLEGDTEKIKDWLFEARDGLLTIAFVGMGGLGKTTLAQKVFND

KRVEDHLERRIWVSVSQTFTEEQVMRSILRSLGDACVGDDQCELLRKINQ

YLLGKRFLIVMDDVWSWDNAWWQKIYTGLPKGNGSTVIVTTRNELVARKM

GVTEARIHWPKFLNEHYSWLLFRKIAFAGSAGECHFPELEDVGKEIVEKC
```

```
-continued
KGLPLAIKAVGGVMLCKPSYYHEWRRISNHFRDELKENDDSVMASLQLSY

DELPPYLKSCFLCFSLFPEDCVIPKDQLIRWWIGEGFIPLRSGRLSTEVG

EDCFSQLSNRCLIEVVDKAYNGVIHTCKMHDMVRDLVIKLAEDDAFFTPA

DATCRHLGIKSEMNWKQLLSNQKLRALLTTTKSGEVNKIHSDIAKKLCKS

RHLQVLDLSKSIFDVPLSSLLEGIGSAKQLTYLSLSNTHPMIGVPASISK

LEKLQILDFSYCQNMKMLPSCVLTFEELAVLDVNNCGSLEYLPKGLSRLS

NLQVLLGFKPAKLSQPGGCRIAELRSLTRLRTLSLRLTENEEIGDDEGNA

LVDLQELQFLTISCFGSQDNGLATKLGRLYPPRQLHELILKFYPSKTSPE

WLNPNLSPMLRYLSIISGDITQMHENFWGDGSTAWKIEGLMLESLSDLRL

EWSAMHQVMPSLRILKVSWCPELESFPIEDAGFRGGLWKKEEHRN
```

The plant may be monocotyledonous or dicotyledonous. Target plants include, but are not limited to, the following: cereals (for example, wheat, barley, rye, oats, rice, maize, sorghum and related crops); grapes; beet (sugar beet and fodder beet); pomes, stone fruit and soft fruit (mango, kiwi, apples, pears, plums, peaches, almonds, cherries, strawberries, raspberries and black-berries); leguminous plants (beans, lentils, peas, soybeans); oil plants (rape or other Brassicas, mustard, poppy, olives, sunflowers, safflower, flax, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, peppers, potatoes, paprika); lauraceae (avocados, cinnamon, camphor); or plants such as maize, cassava, nuts (walnut), coffee, sugar cane, tea, vines, hops, turf, bananas and natural rubber plants, as well as ornamentals (flowers, shrubs, broad-leaved trees and evergreens, such as conifers). In some embodiments, the plant may be susceptible to infection by one or more species of *Xanthomonas* (e.g., one or more species of *Xanthomonas*) without the exogenous polynucleotide. In some cases the plant may be a hybrid. In some cases, the introduction of the exogenous polynucleotide may provide resistance to infection by other *Xanthomonas* species, e.g., *Xanthomonas gardneri*, *Xanthomonas perforans*, *Xanthomonas euvesicatoria*, *Xanthomonas oryzae* pv *oryzae*, *Xanthomonas oryzae* pv. *oryzicola*, *Xanthomonas hortorum*, *Xanthomonas campestris*, *Xanthomonas axonopodis*, *Xanthomonas citri*, *Xanthomonas arboricola*, *Xanthomonas asicola*, *Xanthomonas fragariae*, and/or *Xanthomonas sacchari*. Other bacterial pathogens that contain a YopJ effector include, but are not limited to: *Ralstonia solanacearum*, *Acidovorax citrulli*, *Acidovorax konjaci*, *Brenneria goodwinii*, *Pseudomonas amygdali*, *Pseudomonas syringae*, *Pseudomonas coronafaciens*, *Pseudomonas coronafaciens*, and *Erwinia mallotivora*.

In some embodiments, the plant may be a tomato, pepper, citrus, strawberry, walnut, onion, melon, potato, eggplant, banana, geranium, rose, soybean, rice, brassica, or cassava. In particular embodiments, the plant may be a tomato plant that comprises an exogenous polynucleotide encoding the *Solanum pennellii* JIM2 polypeptide of SEQ ID NO: 2.

Methods for making transgenic plants are very well known in the art, as are the choices for promoters and other regulatory regions (see, e.g., US20160076050, US20170218386 and US20160208279). As such, the present plants may be readily implemented by adapting any suitable method. In some embodiments, the exogenous polynucleotide is operably linked to a promoter. The promoter can be exogenous to the plant or endogenous to the plant. In some embodiments, the plant may be made by replacing a coding sequence in the genome of the plant with the exogenous polynucleotide.

Also provided is a tomato (*Solanum lycopersicum*) plant comprising an exogenous polynucleotide encoding a polypeptide that is at least 80% (at least 85%, at least 90%, at least 95%, at least 98% or 100%) identical to the *Nicotiana benthamiana* ZAR1 polypeptide of SEQ ID NO: 3 or the *Solanum pennellii* ZAR1 polypeptide of SEQ ID NO: 4, wherein the tomato plant is resistant to bacteria that have XopJ4-like effector such as *Xanthomonas*. In these embodiments, the tomato plant may have enhanced resistance to at least one species of *Xanthomonas*, relative to a control plant that is otherwise identical to the plant but does not contain the exogenous polynucleotide. The amino acid sequence of the *Solanum pennellii* ZAR1 polypeptide (SEQ ID NO: 4) is shown below:

```
MVDAVVTVFLEKLLNVLTEESRFLSQHRQQFEKLKNELLFMQSFLKDAER

LKRKHTTLKTVMACLRDLIFEAEEILEDCQNQSADSDGSTRFSTRLHPKR

LSHRHQTGKRLSEINDKITEIKQNISTYLGVPLMKEGSMEAHDNLMTRWT

SSLYDHTQVVGLEGDTEKIKDWLFEASDGLLAVAFVGMGGLGKTTLAQKV

FNERSMENHFERRIWVSVSQTFTEEQVMRSILKTLGDACIGDDQGELLRK

INQYLLGKRFLIVMDDVWSLDNAWWQKIYSGLPKGNGSSVIVTTRNELVA

RKMGVTEARTHWPKFLNEHYSWLLFRKIAFAATAGECDFPELEDVGKEIV

EKCKGLPLAIKAVGGVMLCKPPYYHEWRRIADHFRDELKENDNSVMASLQ

LSYDELPPYLKSCFLCFSLFPEDCVILKDQLIRWWIGESFIPLRSGRLST

EVGEDCFSQLSNRCLIEVVDKAYNGVIHTCKMHDMVRDLVIKIADDDSFS

TPSDANCRHLGINSAMNGKQLLSNRKLRALLTTTKSGEVNKIPSDIAKKF

CNSRHLQVLDLSKSIFDVPLSSLLEGIGSARQLAYLSLSNTHPLIGVPDS

ISNLEKLQILDFSYCQNMKMLPSCVLTFVELAILDLNHCGSLEYLPKGLS

KLSNLQVLLGFKPAKLSQRGGCRISELRSLTRLRRLSLRLTQDEEIGDDE

GNALIGLQELQFLTISCFDSQDDGLVTKLGKLYPPRQLHELILKFYPGKI

SPEWLNPTSLPMLRYMSIVSGDMKEMHDNFWGDHSTFWKIEGLMLEALTD

LRLEWSAINRVMPSLRILKASWCPEVEAFPIEDAGFRGGLWKKEEHSHRC
```

The XopJ4 effector or a YopJ family effector that is recognized by ZAR1 and JIM2, can be selected from XopJ4, PopP1, AvrRxv, AvrBST, and XopJ, for example.

In any embodiment, the plant may be a transgenic plant, meaning that the exogenous polynucleotide has been introduced from the outside, or it may have been made by altering the sequence of a pre-existing gene. Alternatively, in any embodiment, the plant may be cisgenic, meaning that the exogenous polynucleotide has been bred into the plant from a closely related species.

Also provided is a seed of a plant described above. These seeds may be made by selfing the plant or crossing the plant with another plant of the same species to produce, e.g., hybrid seed.

Also provided is a population of at least 100 of the plants, e.g., at least 1,000, or at least 10,000 of the plants, growing in a field.

Also provided is a method for enhancing the resistance of a plant to a bacterial pathogen that contains a YopJ effector, e.g, at least one species of *Xanthomonas* (such as *Xanthomo*- nas *perforans*). In some embodiments, this method may comprise: (a) introducing an exogenous polynucleotide encoding JIM2 polypeptide into a plant cell that is from a plant that is susceptible to infection by the pathogen, e.g., *Xanthomonas* and (b) regenerating a transgenic plant from the plant cell. As noted above, in some embodiments, the JIM2 polypeptide may be at least 80% (e.g. at least 85%, at least 90%, at least 95%, at least 98% or 100%) identical to the *Nicotiana benthamiana* JIM2 polypeptide (SEQ ID NO: 1) or *Solanum pennellii* JIM2 polypeptide (SEQ ID NO: 2). This method may further comprise introducing an exogenous polynucleotide encoding a ZAR1 polypeptide into the plant. In these embodiments, the ZAR1 polypeptide may be at least 80% (e.g. at least 85%, at least 90%, at least 95%, at least 98% or 100%) identical to the *Nicotiana benthamiana* ZAR1 polypeptide (SEQ ID NO: 3).

As noted above, methods for making plants are very well known in the art, as are the choices for promoters and other regulatory regions (see, e.g., US20160076050, US20170218386 and US20160208279). As such, the present plants may be readily implemented by adapting any suitable method.

Examples

Aspects of the present teachings can be further understood in light of the following examples, which should not be construed as limiting the scope of the present teachings in any way.

In this study, a forward genetic screen was used to identify components of the XopJ4 perception pathway in the model plant *N. benthamiana*. This effort resulted in the identification of an NLR protein, NbZAR1, with homology to the *Arabidopsis thaliana* protein ZAR1 (AtZAR1). A subsequent reverse genetic screen identified an RLCK XII gene also required for the perception of XopJ4 which was named XOPJ4 IMMUNITY 2 (JIM2). These genes mediate recognition of XopJ4 as well as other YopJ-family effector proteins and can therefore be used to develop crop varieties with resistance against bacterial pathogens containing these effectors.

Materials and Methods

Genetic Mapping in *Nicotiana benthamiana* Using High-Throughput Sequencing

The *N. benthamiana* zar1-1 mutant was backcrossed to the wild type and the F1 progeny were selfed to create an F2 mapping population. F2 plants were phenotyped by transient expression of XopJ4 using *Agrobacterium* and placed into two separate pools, based on the presence or absence of a cell death response, prior to genomic DNA extraction. Illumina DNA sequencing was performed using one HiSeqX lane with 150 bp paired-end reads for each pool. The reads were mapped to the *N. benthamiana* reference genome (Naim et al., 2012) and SNPs were identified using GATK (DePristo et al., 2011). The SNPs were filtered for mapping quality, possibility of being caused by EMS, and having a large difference in frequency between the mutant and wild type pools (>0.25).

Transient Expression

*Agrobacterium tumefaciens* strain GV3101 was used for transient expression. The binary plasmids pE1776 (with OCS promoter and UAS for strong expression) (Ni et al., 1995) and pORE E4 (Coutu et al., 2007) were used as expression vectors for the desired genes. The primer sequences used for cloning are listed in Table 1 below. To construct the VIGS-resistant version of JIM2, the codon usage of the region targeted by the JIM2 VIGS construct was altered while conserving the predicted amino acid sequence (FIG. 12). This sequence was subsequently fused to the rest of the JIM2 coding sequence and cloned into a vector for transient expression. The plasmids were transformed into *Agrobacterium* and cultures were grown overnight in LB media with appropriate selection (rifampicin 100 µg/mL, gentamycin 25 µg/mL, kanamycin 50 µg/mL). The cultures were centrifuged, suspended in infiltration buffer (10 mM $MgCl_2$, 10 mM MES pH 5.6), diluted to the appropriate $OD_{600}$ and infiltrated into leaf tissue using a needleless syringe. *Xanthomonas* gene knockout and complementation For the knockout of XopJ4 in *Xanthomonas perforans* 4B, 1046 bp upstream and 1127 bp downstream of XopJ4 was cloned into the pLVC18 plasmid containing a SacB counter-selectable marker (Lindgren et al., 1986). This plasmid was conjugated into *Xanthomonas perforans* already lacking the XopQ and AvrBsT genes (Schwartz et al., 2015) and selected on NYG (0.5% peptone, 0.3% yeast extract, 2% glycerol) plates containing tetracycline (10 µg/mL). Colonies were screened for a single crossover event at the target locus by PCR. Positive colonies were grown overnight and plated on NYG plates with 5% sucrose to select for a second crossover event. Colonies were again screened by PCR to obtain XopJ4 deletion strains. For complementation, the XopJ4 gene including the promoter and terminator was cloned onto the plasmid pVSP61 (obtained from William Tucker, DNA Plant Technology, Oakland CA). This plasmid, which can replicate in *Xanthomonas*, was conjugated into *Xanthomonas perforans* and selected for with 25 µg/mL kanamycin.

| SEQ ID | Sequence | Purpose |
| --- | --- | --- |
| 5 | TGGTCTCCGAGCATGGTGGACGCAGTG | Forward SlZAR1 |
| 6 | TGGTCTCCTTGGTCAACACCTATGGCTATATTC | Reverse SlZAR1 |
| 7 | TGGTCTCCGAGCATGGTGGACGCTGTTGTAAC | Forward AtZar1 |
| 8 | TGGTCTCCTTGGTCAGGTTCTGTGCAATG | Reverse AtZar1 |
| 9 | TGGTCTCCGAGCATGAGCAAGAACAATAAGAAG | Forward AtZed1 |
| 10 | TGGTCTCCTTGGTCAAGAGAGTTTCTCAATCAA | Reverse AtZed1 |
| 11 | TGGTCTCCGAGCatgggaaatgtatgogtc | Forward PsHopZ1a |
| 12 | TGGTCTCCTTGGttagcgctgctcttcg | Reverse PsHopz1a |

-continued

| SEQ ID | Sequence | Purpose |
|---|---|---|
| 13 | AAGCCTCGGTCTCCGAGCATGGATTGCATAAAGAAGATGTG | Forward part1 NbJIM2 |
| 14 | AAGCCTCGGTCTCCAAGCGCTGGATATCTGAATTCCAAAC | Reverse part1 NbJIM2 |
| 15 | AAGCCTCGGTCTCCGCTTgtatacgaggacgcg | Reverse part2 NbJIM2_VigsResist |
| 16 | AAGCCTCGGTCTCCCGAAgtatcctggtatccagataagatc | Forward part2 NbJIM2_VigsResist |
| 17 | AAGCCTCGGTCTCCTTCGATCCAGAGTACCAATCTT | Forward part3 NbJIM2 |
| 18 | AAGCCTCGGTCTCCTTGGTTACTCAAATTGCAGGATCTTTC | Reverse part3 NbJIM2 |
| 19 | AAGCCTCGGTCTCCAAAGCGATGGATTCCGGCATAGT | Forward VIGS GUS |
| 20 | AAGCCTCGGTCTCCTTGGTAAGCTTGCATGCCTGCA | Reverse VIGS GUS |
| 21 | AAGCCTCGGTCTCCGAGCAGCTGAAGAAAGAGCAGTAT | Forward RLCKXII-1 (Nbv5tr6201919) |
| 22 | AAGCCTCGGTCTCCTTGGTAAGCACACTCTTGAGATGA | Reverse RLCKXII-1 |
| 23 | AAGCCTCGGTCTCCGAGCATACACCTGCAACAGACATA | Forward RLCKXII-2 (Nbv5tr6223390) |
| 24 | AAGCCTCGGTCTCCTTGGCGCAATCTATTTTCCCAAGA | Reverse RLCKXII-2 |
| 25 | AAGCCTCGGTCTCCGAGCGCACTAGTGTATGAAGATGC | Forward RLCKXII-4 (JIM2) (Nbv5tr6220632) |
| 26 | AAGCCTCGGTCTCCTTGGATAGCCAGGAATCCAAATCA | Reverse RLCKXII-4 (JIM2) |
| 27 | AAGCCTCGGTCTCCGAGCAGAGTTAACCATGAGGGAAA | Forward RLCKXII-3 (Nbv5tr6217417) |
| 28 | AAGCCTCGGTCTCCTTGGAGAAGACACTCCATTGTAGG | Reverse RLCKXII-3 |
| 29 | atactgcaggagctcGGTACCATGGTGGATGCGGTGGTC | Forward NbZAR1, into pORE E4 Kpnl, PvuI gibson |
| 30 | tgccaaatgtttgaacgatcgTCAGTTCCTATGTTCTTCCTTC | Reverse NbZAR1, into pORE E4 Kpnl, PvuI gibson |
| 31 | CTGTTTGCGAGACTTAATCTTTG | Sequencing NbZAR1 |
| 32 | GCTCAGAAAGTCTTCAATGACAA | Sequencing NbZAR1 |
| 33 | TTCTTGGCAATGTCGGAATG | Sequencing NbZAR1 |
| 34 | GGAAGCAACTATTGAGCAATCA | Sequencing NbZAR1 |
| 35 | GCTTATGTTTTTCAATCTCTGGAC | Sequencing NbZAR1 |
| 36 | GTTTCTTTCACTTGCTCCTT | Sequencing NbZAR1 |
| 37 | TTCTCATGACTTGTTCCTCA | Sequencing NbZAR1 |
| 38 | GAATGGCATACGGGACG | forward genotyping XpΔXopJ4 knockout |
| 39 | ATTGCGGAGAGTTATCAGAA | reverse genotyping XpΔXopJ4 knockout |
| 40 | CGCGAAAATGTTCGTCAAG | reverse genotyping XpΔXopJ4 knockout |
| 41 | TTTGTACAAAAAAGCAGGCTCCGCGGCGGGACGATCTGGGCACT | forward 5' XpXopJ4 (Complementation and KO fusion) |

| SEQ ID | Sequence | Purpose |
|---|---|---|
| 42 | GACTCAACGCATGACGAATGGATCCTTCATCGATCAAGTCCGTATAA | reverse for 5' XpXopJ4 KO fusion |
| 43 | TACGGACTTGATCGATGAAGGATCCATTCGTCATGCGTTGAGTC | forward for 3' XpXopJ4 KO fusion |
| 44 | TACAAGAAAGCTGGGTCGGCGCGCC CAGAAAGCCGACGCTGCT | reverse 3' XpXopJ4 (Complementation and KO fusion) |
| 45 | GTGTATAGATTCCCGCTGAA | Forward primer for sequencing NbJIM2 |
| 46 | TCTTCCATATTTGGCGAGTC | Forward primer for sequencing NbJIM2 |
| 47 | TCTCCACTGAGTCTGAAAAC | Reverse primer for sequencing NbJIM2 |
| 48 | ATGGTCTCCTTGGGCCCATCCTTTCTTTTATGAACA | SpZAR1 part 1 forward (BsaI cloning) |
| 49 | ATGGTCTCTGAGACCTATCAGTGCATTCC | SpZAR1 part 1 reverse (BsaI cloning) |
| 50 | ATGGTCTCCTCTCCAAGAACTTCAATTCT | SpZAR1 part 2 forward (BsaI cloning) |
| 51 | ATGGTCTCCGTCAATTTATGTAACGCTCTCT | SpZAR1 part2 reverse (BsaI cloning) |
| 52 | AATGTACTGGGGTGGTTTTGGGCCCACCCCAAAATTTAGCTAATCG | SpJIM2 forward (Gibson cloning ApaI, HpaI) |
| 53 | AGTCAAATTTTCCGTGATAGTTAACAGTGGACAAGTCAACCTATT | SpJIM2 reverse (Gibson cloning ApaI, HpaI) |

Bacterial Growth Assays and Visible Immune Responses

Xanthomonas liquid cultures were grown in NYG media with selection overnight. Cells were collected by centrifugation, washed once and suspended in 10 mMV MgCl$_2$ to an OD$_{600}$ of 0.0001. Plant leaves were infiltrated by needleless syringe. For the growth assay, punches were collected from infiltrated leaf tissue at 0 and 6 days post infiltration, homogenized in 10 mM MgCl$_2$ and serially diluted prior to plating on NYG plates with rifampicin (100 µg/mL) and cycloheximide (50 µg/mL). The plates were incubated at 30° C. for two days and colony counts were obtained to determine the colony forming units for each sample. For visual disease symptoms, the same inoculation conditions were used but the disease was allowed to develop for 14 days before the leaves were photographed. For Ralstonia solanacearum disease assays a cut petiole inoculation assay was performed as previously described (Khokhani et al., 2018). Briefly, an overnight Ralstonia solanacearum culture was spun down, washed, and resuspended in water. The petiole of the first leaf was cut approximately two centimeters from the stem. Bacterial solution (2 µL, OD$_{600}$ of 0.005) was pipetted onto the cut petiole surface and disease symptoms were photographed at ten days post infiltration.

Viral-Induced Gene Silencing

For VIGS, approximately 300 bp of the target gene was cloned into the TRV2 vector (Liu et al., 2002). This vector was transformed into Agrobacterium tumefaciens GV3101. The resulting Agrobacterium strain was grown overnight and co-infiltrated with another Agrobacterium strain harboring the TRV1 vector at an OD$_{600}$ of 0.2 each by needleless syringe. Plants were infiltrated at approximately four weeks old and used for transient assays two to four weeks after infiltration.

Generation of Tomato Expressing ZAR1 and JIM2

The Solanum pennellii alleles of ZAR1 and JIM2 were cloned with native promoters and terminators. The Solanum pennellii ZAR1 gene was cloned in two pieces using primers with sequences ATGGTCTCCTTGGGCC-CATCCTTTCTTTTATGAACA (SEQ ID NO:54), ATGGTCTCTGAGACCTATCAGTGCATTCC (SEQ ID NO: 55), ATGGTCTCCTCTCCAAGAACTTCAATTCT (SEQ ID NO: 56), and ATGGTCTCCGTCAATT-TATGTAACGCTCTCT (SEQ ID NO: 57) into a derivative of the pORE E4 vector. The Solanum pennellii JIM2 gene was amplified and used for Gibson cloning into this plasmid with the restriction enzymes ApaI and HpaI using the primers with sequences AATGTACTGGGGTGGTTTTGGGCCCACCCCAAAAT-TTAGCTAATCG (SEQ ID NO:58) and AGTCAAAT-TTTCCGTGATAGTTAACAGTGGACAAGTCAACCT-ATT (SEQ ID NO: 59). The plasmid was transformed into Agrobacterium tumefaciens and tomato transgenics were generated as previously described (McCormick et al., 1986). Tomato transformants were confirmed by genotyping with PCR to test for the presence of the transgene.

Results

Figure 3:
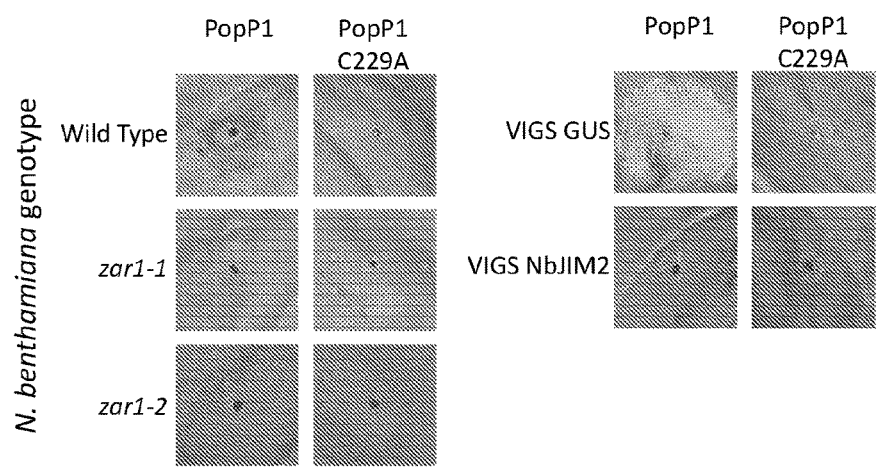
FIG. 3. PopP1 perception in zar1 mutants and JIM2-silenced plants. PopP1 wild type and the C229A catalytic mutant were transiently expressed using *Agrobacterium* in wild type, zar1-1 and zar1-2 mutants (left) and wild type plants silenced for GUS (as a negative control) or NbJIM2 (right). The *Agrobacterium* was infiltrated at an $OD_{600}$ of 0.5 and plants were imaged at four days post infiltration. The data in this figure indicates that recognition of the *Ralstonia solanacearum* effector protein PopP1 is dependent on NbZAR1 and NbJIM2.

Identification of Two Allelic *N. benthamiana* Mutants Impaired in XopJ4 Recognition A forward genetic screen of 2,000 M2 plants from an EMS-mutagenized population of *N. benthamiana* for individuals lacking a cell death response to transiently expressed XopJ4. Two allelic mutants were identified that failed to respond to transiently-expressed XopJ4 (FIG. 1). A mapping by sequencing approach was used to identify the genetic basis of these mutants. Both mutants were found to have mutations in the gene Nbv5tr6207061, named NbZAR1 after its *Arabidopsis* homolog. The mutants, named zar1-1 and zar1-2, had single nucleotide polymorphisms resulting in Q195Stop and T191I changes in the predicted amino acid sequence of NbZAR1 respectively. In addition to lacking an immune response to transiently expressed XopJ4, these mutants were deficient for an immune response to other YopJ-family effector proteins including XopJ, AvrRxv, AvrBsT and PopP1 (FIG. 1, FIG. 3).

Figure 2:
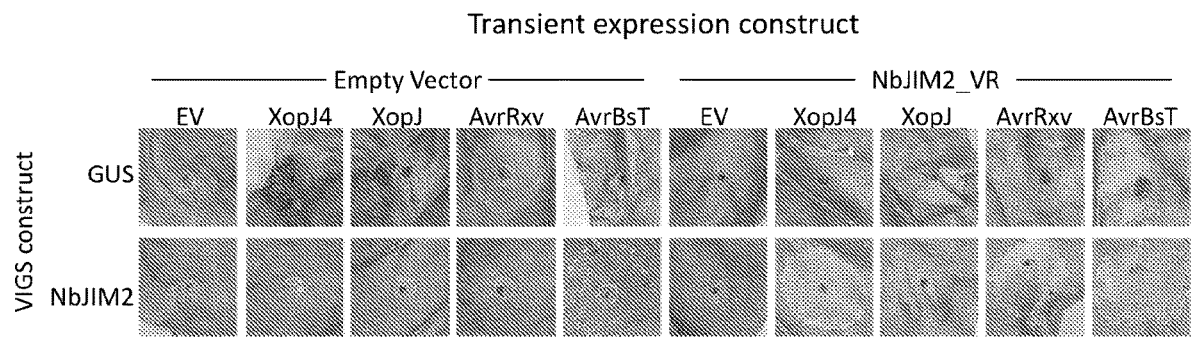
FIG. 2. *Xanthomonas* effector proteins from the YopJ family were transiently expressed with an empty vector (left) or the codon-altered VIGS-resistant NbJIM2 protein (NbJIM2_VR, right) in *N. benthamiana* plants silenced for GUS (as a negative control, top) or the native NbJIM2 gene (bottom). *Agrobacterium* was infiltrated at an $OD_{600}$ of 0.5 total and the plants were photographed at three days post infiltration. The data in this figure indicate that the NbJIM2 gene is required for perception of XopJ4, XopJ and AvrRxv in *N. benthamiana*. As observed for NbZAR1, disruption of NbJIM2 reduces but does not eliminate the response to AvrBsT indicating that NbJIM2 mediates perception of AvrBsT but that there may be an NbJIM2-independent recognition pathway.
Figure 4:
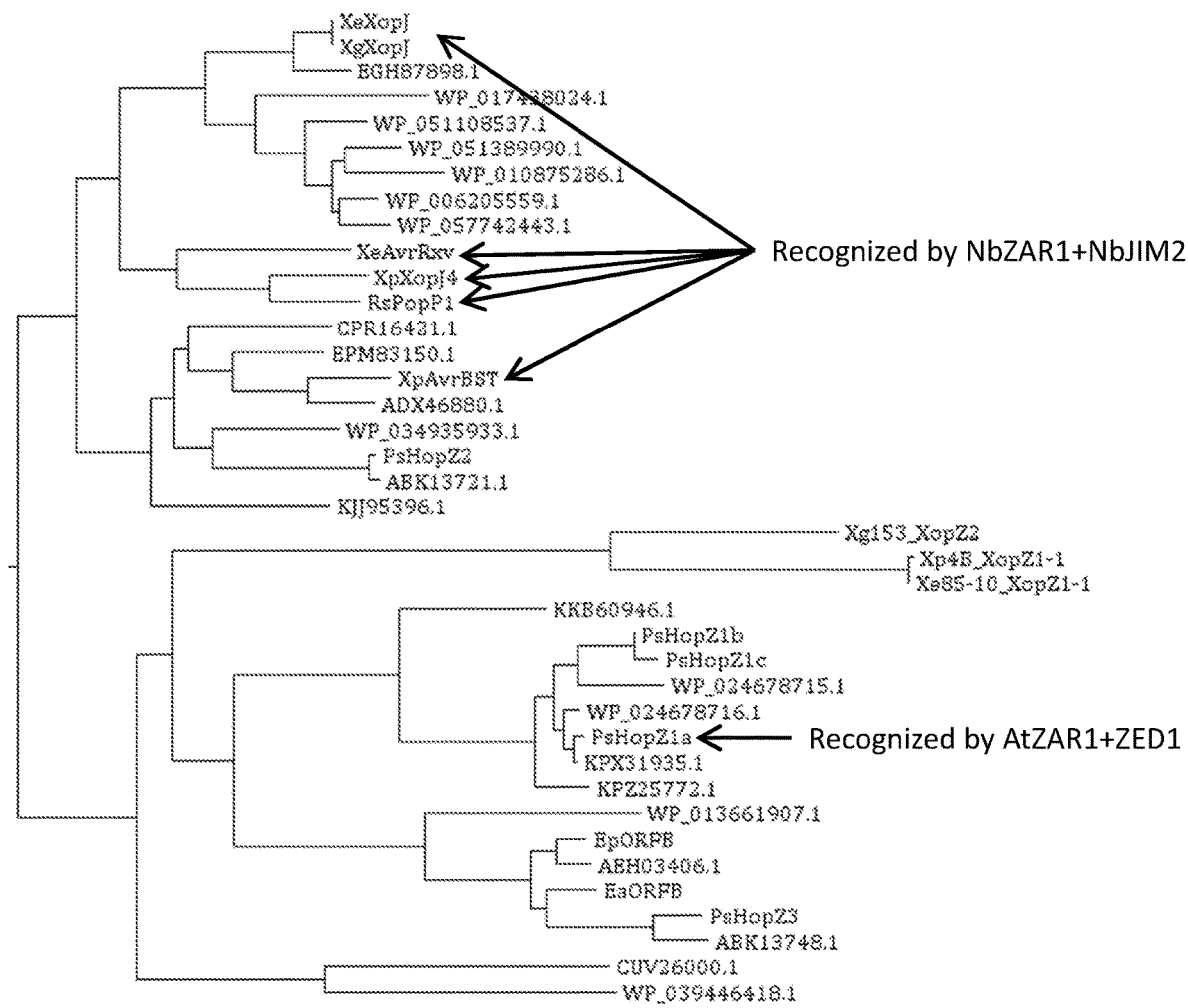
FIG. 4. Phylogenetic tree of YopJ family effector proteins. The protein sequences from various plant pathogen YopJ-family effectors were used to construct a phylogenetic tree. The five YopJ effector protein sequences that were observed to be recognized by NbZAR1 and NbJIM2 are in a separate clade from HopZ1a, which is recognized by AtZAR1 and ZED1. The data in this figure shows that the YopJ effectors perceived by NbZAR1 and NbJIM2 fall within a clade that is distinct from HopZ1a. This suggests that the effector proteins within the top clade can be perceived by NbZAR1 and NbJIM2, whereas those in the lower clade containing HopZ1a may not be. This indicates the functional divergence between the AtZAR1/ZED1 and NbZAR1/NbJIM2 recognition pathways.

Identification of JIM2, a Receptor-Like Cytoplasmic Kinase Required for XopJ4 Perception The ZAR1 protein from *Arabidopsis thaliana* interacts with several RLCK XII proteins which are required for the recognition of specific bacterial effectors including ZED1 (HopZ1a recognition) (Lewis et al., 2013), RKS1 (AvrAC recognition) (Wang et al., 2015) and ZRK3 (HopF2a recognition) (Seto et al., 2017). This suggested that an RLCK XII protein may be involved in the ZAR1-mediated recognition of XopJ4. Four RLCK XII genes were identified in the genome of *N. benthamiana* and targeted for silencing by Viral Induced Gene Silencing (VIGS). The silencing of one particular RLCK XII, hereafter named XOPJ4 IMMUNITY 2 (JIM2), compromised the ability of the plant to recognize XopJ4, XopJ, AvrRxv, AvrBsT and PopP1 (FIG. 2, FIG. 3). The YopJ-family effector proteins recognized by NbZAR1 and JIM2 form a clade that is distinct from PsHopZ1a, which is recognized by AtZAR1 and ZED1 (FIG. 4).

*N. benthamiana* Zar1-1 and Zar1-2 are Deficient for Resistance Against *X. perforans* Expressing XopJ4

Figure 5:
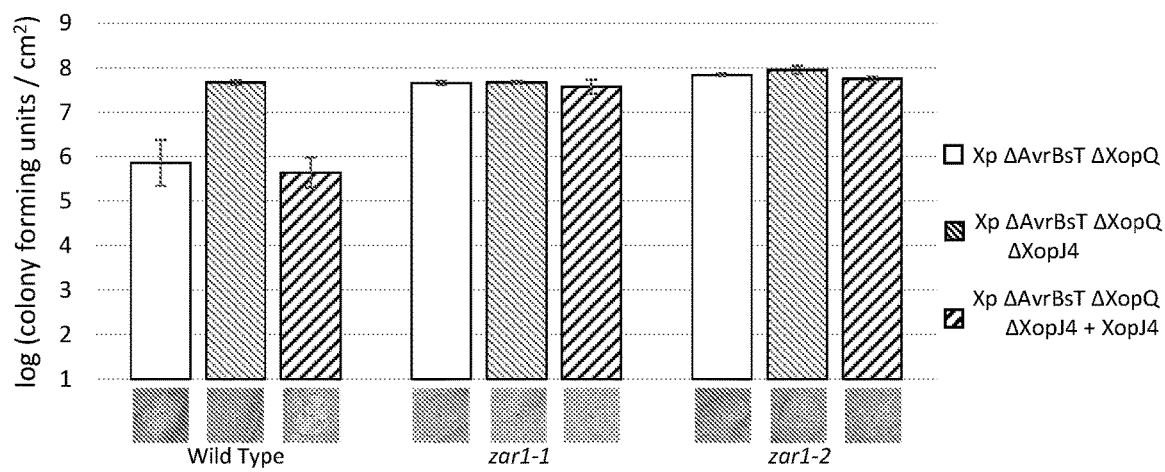
FIG. 5. Bacterial growth and visible immune response to *Xanthomonas perforans*. *Nicotiana benthamiana* wild type and zar1 mutants were infiltrated with the indicated genotype of *X. perforans* at $OD_{600}$=0.0001. Bacterial growth was assayed at six days post infiltration and the visible immune response was photographed at seven days post infiltration. Error bars indicated standard deviation from three biological replicates. The data in this figure shows that perception of XopJ4 mediated by NbZAR1 correlates with resistance to the *Xanthomonas* pathogen containing this effector protein. Δ indicates that the following effector gene was knocked out in that strain of *Xanthomonas*.

To test whether the avirulence activity of XopJ4 was compromised in the zar1 mutants, the XopJ4 gene was knocked out in an *X. perforans* (Xp) strain already deficient for XopQ and AvrBsT, as these two effectors trigger avirulence responses in *N. benthamiana* (Schwartz et al., 2015). This knockout strain, along with parental and complemented strains, was infiltrated into *N. benthamiana* leaves at a low inoculum and bacterial growth was assayed by measuring colony forming units at six days post infiltration. Growth of Xp ΔAvrBst ΔXopQ ΔXopJ4 was found to be approximately 100-fold greater in wild type *N. benthamiana* leaf tissue compared to Xp ΔAvrBst ΔXopQ and the complemented strain Xp ΔAvrBst ΔXopQ ΔXopJ4+XopJ4 (FIG. 5). This indicates that XopJ4 triggers an avirulence response on wild type *N. benthamiana*. No avirulence effect of XopJ4 was observed on the zar1-1 and zar1-2 mutants as a similar high level of bacterial growth was observed regardless of the presence of XopJ4 (FIG. 5). Consistent with the growth phenotypes, a visible immune response was observed in wild type *N. benthamiana* plants infiltrated with Xp expressing XopJ4 (FIG. 5). This response was not observed in the zar1-1 and zar1-2 mutants.

AtZAR1 and SlZAR1 Fail to Complement the *N. benthamiana* Zar1-1 Mutant

Figure 6:
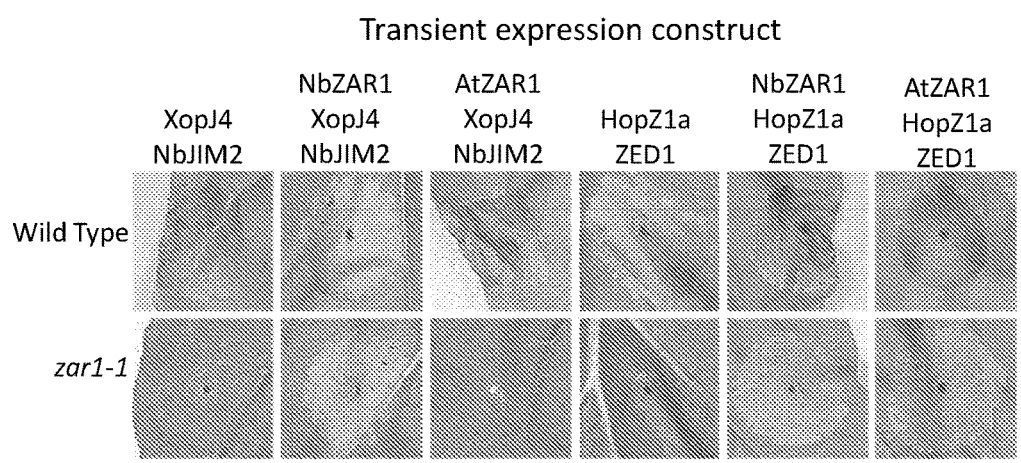
FIG. 6. AtZAR1 complementation of zar1-1. *Agrobacterium* was used to transiently express the indicated genes in leaf tissue of wild type *Nicotiana benthamiana* and the zar1-1 mutant. The *Agrobacterium* was infiltrated at an $OD_{600}$ of 0.3 for each construct and the plants were imaged at two days post infiltration. The data in this figure shows that the previously known gene AtZAR1 is not able to mediate perception of XopJ4 and therefore has distinct functionality from NbZAR1.

To test whether AtZAR1 is functionally equivalent to NbZAR1, AtZAR1 was transiently expressed in the zar1-1 mutant along with JIM2 and XopJ4. Whereas transient expression of NbZAR1 was sufficient to restore XopJ4 recognition in the zar1-1 mutant, expression of AtZAR1 was not (FIG. 6). In contrast, transient expression of AtZAR1 in zar1-1 was able to complement the immune response triggered by co-expression of ZED1 and HopZ1a. The inability of AtZAR1 to complement the XopJ4 perception defect in zar1-1 plants indicates a partial functional divergence between NbZAR1 and AtZAR1.

Figure 7:
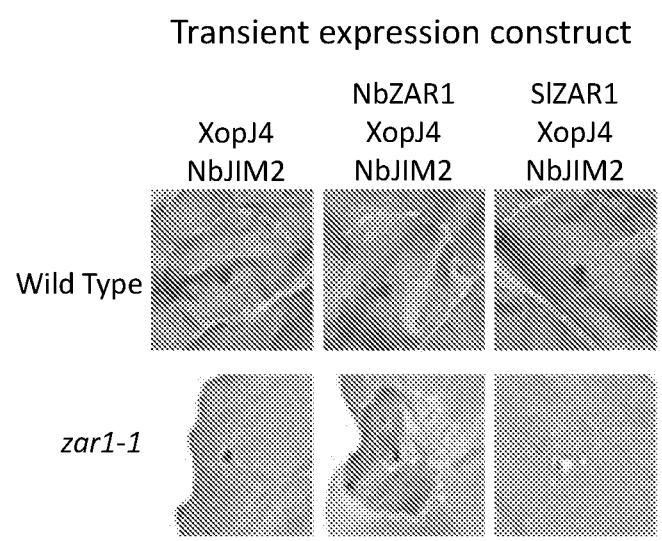
FIG. 7. Functional complementation testing of SlZAR1. The indicated genes were transiently expressed using *Agrobacterium* in *Nicotiana benthamiana* wild type and the zar1-1 mutant. The plants were infiltrated at an $OD_{600}$ of 0.3 for each construct and imaged at three days post infiltration. The data in this figure shows that SlZAR1 is not able to complement the function of NbZAR1 despite tomato and *N. benthamiana* being closely related.

Tomato (*Solanum lycopersicum*) contains a putative ZAR1 ortholog but is unable to perceive the XopJ4 effector protein (Astua-Monge et al., 2000). SlZAR1 (Solyc02g084890) was cloned and transiently expressed in the zar1-1 mutant to test if this gene can functionally complement NbZAR1 for XopJ4 perception. Transient expression of SlZAR1, JIM2 and XopJ4 failed to trigger a visible immune response in the zar1-1 mutant (FIG. 7). A multiple sequence alignment of ZAR1 proteins from various plant species revealed several missense mutations at conserved sites in the SlZAR1 protein which may make the protein nonfunctional (FIG. 8).

A JIM2 Homolog from *Solanum pennellii* can Complement *N. benthamiana* Plants Deficient for NbJIM2

*Solanum pennellii* was previously known to be able to recognize XopJ4 and be resistant to *Xanthomonas perforans*. A highly conserved ortholog of NbZAR1 was identified in the genome of *S. pennellii* (FIG. 8) but the closest homolog to NbJIM2 has significant sequence divergence. Transient expression of SpJIM2 in an *N. benthamiana* plant deficient for NbJIM2 revealed that SpJIM2 is indeed functional and able to mediate perception of XopJ4 (FIG. 9).

ZAR1 and JIM2 Confer Resistance to *Xanthomonas perforans*

Figure 10:
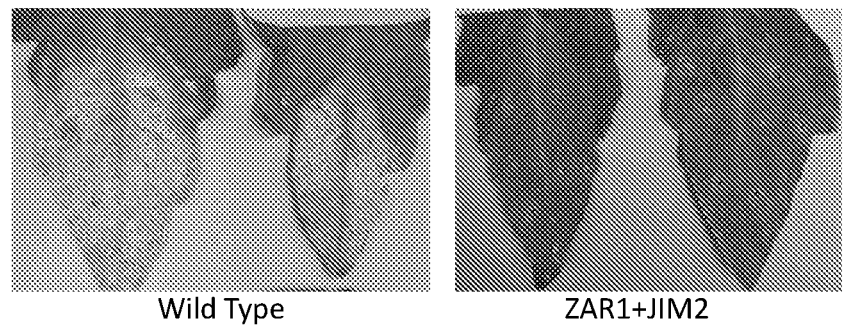
FIG. 10. ZAR1 and JIM2 confer resistance to *Xanthomonas perforans*. The *Solanum pennellii* alleles of ZAR1 and JIM2 were transformed into tomato. To test for disease resistance, a bacterial solution of *Xanthomonas perforans* was infiltrated into leaf tissue at a low inoculum ($OD_{600}$=0.0001). The infiltrated leaves were photographed at 14 days post infiltration to observed visual disease symptoms (A). The wild type tomato (lacking ZAR1 and JIM2) developed severe yellowing and necrotic lesions in the infiltrated region (A, left) whereas the tomato line expressing ZAR1 and JIM2 appeared healthy (A, right). To measure bacterial proliferation, leaf punches were collected at six days post infiltration, homogenized in water, and plated on agar plates. Approximately twenty-five times more colony forming units were detected from wild type than from tomato expressing ZAR1 and JIM2 (B). These results indicate that ZAR1 and JIM2 confer resistance to *Xanthomonas perforans* in tomato. Error bars indicate standard deviation.
Figure 10:
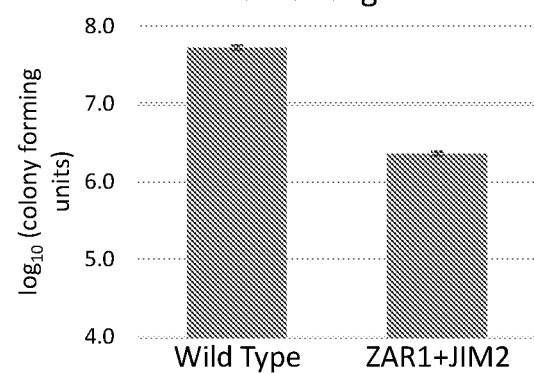

Given that ZAR1 and JIM2 are required for recognition of XopJ4 and resistance to the bacterial pathogen *Xanthomonas perforans* in *Nicotiana benthamiana*, we believed that these genes would work in other plant species to confer resistance to this disease. We transformed ZAR1 and JIM2 from *Solanum pennellii* into tomato. The transformed tomato plants were tested for resistance against *Xanthomonas perforans* by infiltrating a low inoculum of bacteria into leaf tissue. At 14 days post infiltration, wild type tomato leaves had severe disease symptoms as observed by yellow and necrotic lesions in the infiltrated area of the leaves whereas tomatoes expressing ZAR1 and JIM2 appeared healthy (FIG. 10A). Bacterial counts obtained at six days post infiltration indicated that the *Xanthomonas perforans* proliferated to a twenty-five-fold lower bacterial titer on the ZAR1+JIM2 plants than on wild type plants (FIG. 10B). These data indicated that the tomato plants expressing ZAR1 and JIM2 are qualitatively and quantitatively resistant to *Xanthomonas perforans*. This is consistent with resistance being mediated by recognition of the effector protein XopJ4, which is present in *Xanthomonas perforans* strain 4B.

ZAR1 and JIM2 Confer Resistance to *Ralstonia solanacearum*

Figure 11:
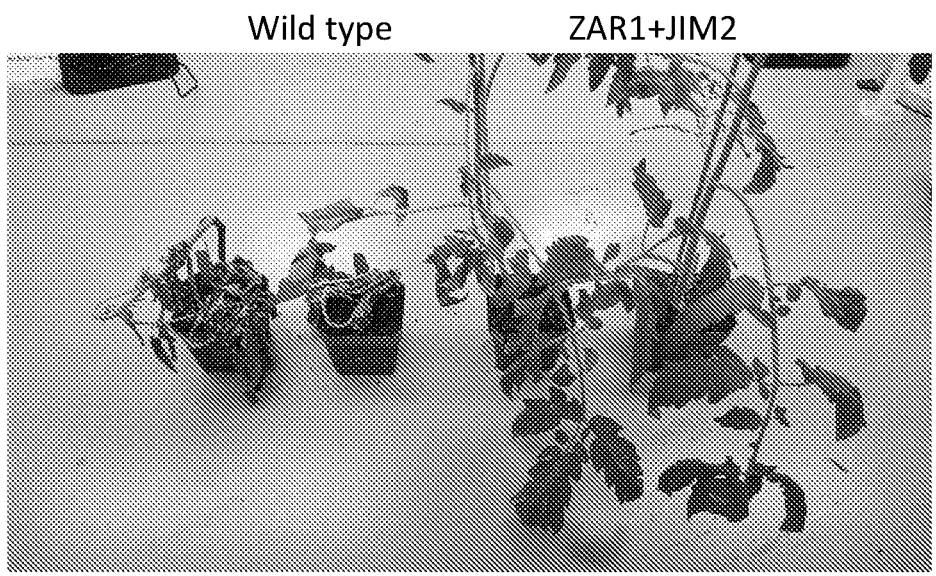
FIG. 11. ZAR1 and JIM2 confer resistance to *Ralstonia solanacearum*. *Ralstonia solanacearum* causes severe wilting of a susceptible tomato variety (left) whereas tomato expressing ZAR1 and JIM2 is resistant (right). The plants were inoculated by placing bacterial solution ($OD_{600}$=0.0005) onto the exposed surface of a cut petiole. The plants were imaged at 10 days post inoculation.

*Ralstonia solanacearum* is a vascular pathogen and that can cause severe wilting in susceptible plants. We hypothesized that expression of ZAR1 and JIM2 would be sufficient to confer resistance to *Ralstonia solanacearum* strains containing PopP1 or similar effectors recognized by ZAR1 and JIM2. To test this, we expressed ZAR1 and JIM2 in a tomato variety that is otherwise susceptible to this pathogen. Wild type tomato and plants expressing ZAR1+JIM2 were infected with *Ralstonia solanacearum* using the cut petiole inoculation method. At ten days post inoculation, wild type plants were severely wilted whereas tomato plants expressing ZAR1+JIM2 appeared healthy (FIG. 11). These results indicate that ZAR1 and JIM2 can be used to confer resistance against *Ralstonia solanacearum*.

REFERENCES

Alfano, J. R., and Collmer, A. (2004). Type III secretion system effector proteins: double agents in bacterial disease and plant defense. *Annu. Rev. Phytopathol.* 42:385-414.

Astua-Monge, G., Minsavage, G. V., Stall, R. E., Vallejos, C. E., Davis, M. J., and Jones, J. B. (2000). Xv4-vrxv4: A New Gene-for-Gene Interaction Identified Between *Xanthomonas campestris* pv. *Vesicatoria* Race T3 and the Wild Tomato Relative *Lycopersicon pennellii. Mol. Plant-Microbe Interact.* 13:1346-1355.

Baudin, M., Hassan, J. A., Schreiber, K. J., and Lewis, J. D. (2017). Analysis of the ZAR1 Immune Complex Reveals Determinants for Immunity and Molecular Interactions. *Plant Physiol.* 174:2038-2053.

Castañeda, A., Reddy, J. D., El-Yacoubi, B., and Gabriel, D. W. (2005). Mutagenesis of all eight avr genes in *Xanthomonas campestris* pv. *campestris* had no detected effect on pathogenicity, but one avr gene affected race specificity. *Mol. Plant. Microbe. Interact.* 18:1306-1317.

Coutu, C., Brandle, J., Brown, D., Brown, K., Miki, B., Simmonds, J., and Hegedus, D. D. (2007). pORE: A modular binary vector series suited for both monocot and dicot plant transformation. *Transgenic Res.* 16:771-781.

DePristo, M. A., Banks, E., Poplin, R., Garimella, K. V, Maguire, J. R., Hartl, C., Philippakis, A. A., del Angel, G., Rivas, M. A., Hanna, M., et al. (2011). A framework for variation discovery and genotyping using next-generation DNA sequencing data. *Nat. Genet.* 43:491-8.

Deslandes, L., Olivier, J., Theulieres, F., Hirsch, J., Feng, D. X., Bittner-Eddy, P., Beynon, J., and Marco, Y. (2002). Resistance to *Ralstonia solanacearum* in *Arabidopsis thaliana* is conferred by the recessive RRS1-R gene, a member of a novel family of resistance genes. *Proc. Natl. Acad. Sci. U.S.A.* 99:2404-9.

Dodds, P. N., and Rathjen, J. P. (2010). Plant immunity: towards an integrated view of plant-pathogen interactions. *Nat. Rev. Genet.* 11:539-548.

Gürlebeck, D., Thieme, F., and Bonas, U. (2006). Type III effector proteins from the plant pathogen *Xanthomonas* and their role in the interaction with the host plant. *J. Plant Physiol.* 163:233-55.

Jones, J. D. G., Vance, R. E., and Dangl, J. L. (2016). Intracellular innate immune surveillance devices in plants and animals. *Science* (80-.). 354:aaf6395.

Khan, M., Subramaniam, R., and Desveaux, D. (2016). Of guards, decoys, baits and traps: Pathogen perception in plants by type III effector sensors. *Curr. Opin. Microbiol.* 29:49-55.

Khokhani, D., Tuan, T., Lowe-Power, T., and Allen, C. (2018). Plant Assays for Quantifying *Ralstonia solanacearum* Virulence. *Bio-Protocol* 8:1-19.

Kim, N. H., Kim, D. S., Chung, E. H., and Hwang, B. K. (2014). Pepper suppressor of the G2 allele of skp1 interacts with the receptor-like cytoplasmic kinase1 and type III effector AvrBsT and promotes the hypersensitive cell death response in a phosphorylation-dependent manner. *Plant Physiol.* 165:76-91.

Kim, B. S., French, E., Caldwell, D., Harrington, E. J., and Iyer-Pascuzzi, A. S. (2015). Bacterial wilt disease: Host resistance and pathogen virulence mechanisms. *Physiol. Mol. Plant Pathol.* 95:37-43.

Lewis, J. D., Wu, R., Guttman, D. S., and Desveaux, D. (2010). Allele-specific virulence attenuation of the *Pseudomonas syringae* HopZ1a type III effector via the *Arabidopsis* ZAR1 resistance protein. *PLoS Genet.* 6:1-13.

Lewis, J. D., Lee, A. H.-Y., Hassan, J. a, Wan, J., Hurley, B., Jhingree, J. R., Wang, P. W., Lo, T., Youn, J.-Y., Guttman, D. S., et al. (2013). The *Arabidopsis* ZED1 pseudokinase is required for ZAR1-mediated immunity induced by the *Pseudomonas syringae* type III effector HopZ1a. *Proc. Natl. Acad. Sci. U.S.A.* 110:18722-7.

Lindgren, P. B., Peet, R. C., and Panopoulos, N. J. (1986). Gene cluster of *Pseudomonas syringae* pv. "*phaseolicola*" controls pathogenicity of bean plants and hypersensitivity of nonhost plants. *J. Bacteriol.* 168:512-522.

Liu, Y., Schiff, M., Marathe, R., and Dinesh-Kumar, S. P. (2002). Tobacco Rar1, EDS1 and NPR1/NIM1 like genes are required for N-mediated resistance to tobacco mosaic virus. *Plant J.* 30:415-429.

Ma, K., and Ma, W. (2016). YopJ Family Effectors Promote Bacterial Infection through a Acetyltransferase Activity. *Microbiol. Mol. Biol. Rev.* 80:1011-1027.

Macho, A. P., and Zipfel, C. (2014). Plant PRRs and the activation of innate immune signaling. *Mol. Cell* 54:263-272.

McCormick, S., Niedermeyer, J., Fry, J., Barnason, A., Horsch, R., and Fraley, R. (1986). Leaf disc transformation of cultivated tomato (<i>*L. esculentum*</i>) using <i>*Agrobacterium tumefaciens*</i> *Plant Cell Rep.* 5:81-84.

Minsavage, G. V., Dahlbeck, D., Whalen, M. C., Kearney, B., Bonas, U., Staskawicz, B. J., and Stall, R. E. (1990). Gene-for-gene relationships specifying disease resistance in *Xanthomonas campestris* pv. *vesicatoria*—pepper interactions. *Mol. Plant-Microbe Interact.* 3:41-47.

Naim, F., Nakasugi, K., Crowhurst, R. N., Hilario, E., Zwart, A. B., Hellens, R. P., Taylor, J. M., Waterhouse, P. M., and Wood, C. C. (2012). Advanced Engineering of Lipid Metabolism in *Nicotiana benthamiana* Using a Draft Genome and the V2 Viral Silencing-Suppressor Protein. *PLoS One* 7.

Narusaka, M., Shirasu, K., Noutoshi, Y., Kubo, Y., Shiraishi, T., Iwabuchi, M., and Narusaka, Y. (2009). RRS1 and RPS4 provide a dual Resistance-gene system against fungal and bacterial pathogens. *Plant J.* 60:218-226.

Ni, M., Cui, D., Einstein, J., Narasimhulu, S., Vergara, C. E., and Gelvin, S. B. (1995). Strength and tissue specificity of chimeric promoters derived from the octopine and mannopine synthase genes. *Plant J.* 7:661-676.

Roden, J., Eardley, L., Hotson, A., Cao, Y., and Mudgett, M. B. (2004). Characterization of the *Xanthomonas* AvrXv4 effector, a SUMO protease translocated into plant cells. *Mol Plant Microbe Interact* 17:633-643.

Sarris, P. F., Duxbury, Z., Huh, S. U., Ma, Y., Segonzac, C., Sklenar, J., Derbyshire, P., Cevik, V., Rallapalli, G., Saucet, S. B., et al. (2015). A plant immune receptor detects pathogen effectors that target WRKY transcription factors. *Cell* 161:1089-1100.

Schwartz, A. R., Potnis, N., Timilsina, S., Wilson, M., Patané, J., Martins, J., Minsavage, G. V., Dahlbeck, D., Akhunova, A., Almeida, N., et al. (2015). Phylogenomics of *Xanthomonas* field strains infecting pepper and tomato reveals diversity in effector repertoires and identifies determinants of host specificity. *Front. Microbiol.* 6:535.

Seto, D., Koulena, N., Lo, T., Menna, A., Guttman, D. S., and Desveaux, D. (2017). Expanded type III effector recognition by the ZAR1 NLR protein using ZED1-related kinases. *Nat. Plants* 3:17027.

Sharlach, M., Dahlbeck, D., Liu, L., Chiu, J., Jiménez-Gómez, J. M., Kimura, S., Koenig, D., Maloof, J. N., Sinha, N., Minsavage, G. V., et al. (2013). Fine genetic mapping of RXopJ4, a bacterial spot disease resistance locus from *Solanum pennellii* LA716. *Theor. Appl. Genet.* 126:601-609.

Stall, R. E., Jones, J. B., and Minsavage, G. V (2009). Durability of resistance in tomato and pepper to xanthomonads causing bacterial spot. *Annu. Rev. Phytopathol.* 47:265-84.

Timilsina, S., Abrahamian, P., Potnis, N., Minsavage, G. V, White, F. F., Staskawicz, B. J., Jones, J. B., Vallad, G. E., and Goss, E. M. (2016). Analysis of sequenced genomes of *Xanthomonas perforans* identifies candidate targets for resistance breeding in tomato. *Phytopathology* 106: PHYTO-03-16-0119-FI.

Wang, G., Roux, B., Feng, F., Guy, E., Li, L., Li, N., Zhang, X., Lautier, M., Jardinaud, M. F., Chabannes, M., et al. (2015). The Decoy Substrate of a Pathogen Effector and a Pseudokinase Specify Pathogen-Induced Modified-Self Recognition and Immunity in Plants. *Cell Host Microbe* 18:285-295.

Wei, C.-F., Kvitko, B. H., Shimizu, R., Crabill, E., Alfano, J. R., Lin, N.-C., Martin, G. B., Huang, H.-C., and Collmer, A. (2007). A *Pseudomonas syringae* pv. tomato DC3000 mutant lacking the type III effector HopQ1-1 is able to cause disease in the model plant *Nicotiana benthamiana*. *Plant J.* 51:32-46.

Whalen, M. C., Wang, J. F., Carland, F. M., Heiskell, M. E., Dahlbeck, D., Minsavage, G. V, Jones, J. B., Scott, J. W., Stall, R. E., and Staskawicz, B. J. (1993). Avirulence gene avrRxv from *Xanthomonas campestris* pv. *vesicatoria* specifies resistance on tomato line Hawaii 7998. *Mol Plant Microbe Interact* 6:616-627.

Williams, S. J., Sohn, K. H., Wan, L., Bernoux, M., Sarris, P. F., Segonzac, C., Ve, T., Ma, Y., Saucet, S. B., Ericsson, D. J., et al. (2014). Structural basis for assembly and function of a heterodimeric plant immune receptor. *Science* (80-.). 344:299-303.

Wulff, B. B. H., Horvath, D. M., and Ward, E. R. (2011). Improving immunity in crops: New tactics in an old game. *Curr. Opin. Plant Biol.* 14:468-476.

Yu, Z. H., Wang, J. F., Stall, R. E., and Vallejos, C. E. (1995). Genomic localization of tomato genes that control a hypersensitive reaction to *Xanthomonas campestris* pv. *vesicatoria* (Doidge) dye. *Genetics* 141:675-682.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

---

That which is claimed is:

1. A tomato plant comprising:

an exogenous polynucleotide encoding a JIM2 polypeptide that is at least 90% identical to the *Nicotiana benthamiana* JIM2 of SEQ ID NO: 1 or the *Solanum pennellii* JIM2 of SEQ ID NO: 2; and exogenous polynucleotide encoding a ZAR1 polypeptide that is at least 90% identical to the *Nicotiana benthamiana* ZAR1 of SEQ ID NO: 3 or the *Solanum pennellii* ZAR1 polypeptide of SEQ ID NO: 4, wherein the plant has enhanced resistance to *Xanthomonas perforans*, relative to a control plant that is otherwise identical to the plant but does not contain the exogenous polynucleotides.

2. The plant of claim 1, wherein:

the JIM2 polypeptide is at least 95% identical to the *Nicotiana benthamiana* JIM2 of SEQ ID NO: 1 or the *Solanum pennellii* JIM2 of SEQ ID NO: 2; and the ZAR1 polypeptide is at least 95% identical to the *Nicotiana benthamiana* ZAR1 of SEQ ID NO: 3 or the *Solanum pennellii* ZAR1 polypeptide of SEQ ID NO: 4.

3. The plant of claim 1, wherein the plant comprises an exogenous polynucleotide encoding the *Solanum pennellii* JIM2 polypeptide of SEQ ID NO: 2.

4. The plant of claim 1, wherein the exogenous polynucleotides are each operably linked to a promoter.

5. The plant of claim 4, wherein the promoters are exogenous to the plant.

6. The plant of claim 4, wherein the promoters are endogenous to the plant.

7. A seed of a plant of claim 1, wherein the seed comprises the exogenous polynucleotide encoding a JIM2 polypeptide and the exogenous polynucleotide encoding a ZAR1 polypeptide.

8. A population of at least 100 plants of claim 1.

9. A method for enhancing the resistance of a tomato plant to at least one species of *Xanthomonas*, comprising:
(a) introducing:
(i) an exogenous polynucleotide encoding a JIM2 polypeptide that is at least 90% identical to the *Nicotiana benthamiana* JIM2 of SEQ ID NO: 1 or the *Solanum pennellii* JIM2 of SEQ ID NO: 2; and
(ii) an exogenous polynucleotide encoding a ZAR1 polypeptide that is at least 90% identical to the *Nicotiana benthamiana* ZAR1 of SEQ ID NO: 3 or the *Solanum pennellii* ZAR1 polypeptide of SEQ ID NO: 4;
into a tomato cell; and
(b) regenerating a transgenic tomato plant from the tomato plant cell.

10. The method of claim 9, wherein the JIM2 polypeptide is at least 95% identical to the *Nicotiana benthamiana* JIM2 of SEQ ID NO: 1 or the *Solanum pennellii* JIM2 of SEQ ID NO: 2; and
the ZAR1 polypeptide that is at least 95% identical to the *Nicotiana benthamiana* ZAR1 of SEQ ID NO: 3 or the *Solanum pennellii* ZAR1 polypeptide of SEQ ID NO: 4.

11. A method for enhancing the resistance of a potato plant to at least one species of *Ralstonia*, comprising:
(a) introducing an exogenous polynucleotide encoding a JIM2 polypeptide that is at least 90% identical to the *Nicotiana benthamiana* JIM2 of SEQ ID NO: 1 or the *Solanum pennellii* JIM2 of SEQ ID NO: 2 into a potato cell; and
(b) regenerating a transgenic potato plant from the potato plant cell; and
(c) selecting said transgenic potato plant or a progeny of the same that contains the exogenous polynucleotide for resistance to *Ralstonia*.

12. The method of claim 11, wherein the JIM2 polypeptide is at least 95% identical to the *Nicotiana benthamiana* JIM2 of SEQ ID NO: 1 or the *Solanum pennellii* JIM2 of SEQ ID NO: 2.

13. The method of claim 11, further comprising collecting seed from said transgenic potato plant or a progeny of the same that contains the exogenous polynucleotide.

* * * * *